United States Patent
Schooley et al.

(10) Patent No.: US 10,562,969 B2
(45) Date of Patent: Feb. 18, 2020

(54) SUBSTITUTION MONOTHERAPY TREATMENT FOR HIV-1 INFECTION EMPLOYING ANTIBODY PRO140

(71) Applicant: CYTODYN INC., Vancouver, WA (US)

(72) Inventors: Robert T. Schooley, La Jolla, CA (US); Nader Z. Pourhassan, Vancouver, WA (US)

(73) Assignee: Cytodyn Inc., Vancouver, WA (US)

( * ) Notice: Subject to any disclaimer, the term of this patent is extended or adjusted under 35 U.S.C. 154(b) by 0 days.

(21) Appl. No.: 15/504,928

(22) PCT Filed: Aug. 20, 2015

(86) PCT No.: PCT/US2015/046160
§ 371 (c)(1),
(2) Date: Jun. 1, 2017

(87) PCT Pub. No.: WO2016/029049
PCT Pub. Date: Feb. 25, 2016

(65) Prior Publication Data
US 2017/0335002 A1    Nov. 23, 2017

Related U.S. Application Data

(60) Provisional application No. 62/192,941, filed on Jul. 15, 2015, provisional application No. 62/039,620, filed on Aug. 20, 2014.

(51) Int. Cl.
*C07K 16/28*  (2006.01)
*A61K 39/395*  (2006.01)
*A61K 39/00*  (2006.01)

(52) U.S. Cl.
CPC ........ *C07K 16/2866* (2013.01); *A61K 39/395* (2013.01); *A61K 2039/505* (2013.01); *A61K 2039/54* (2013.01); *A61K 2039/545* (2013.01); *C07K 2317/24* (2013.01); *C07K 2317/76* (2013.01)

(58) Field of Classification Search
CPC ............................ C07K 16/2866; A61K 39/395
See application file for complete search history.

(56) References Cited

U.S. PATENT DOCUMENTS 7,863,242 B2  1/2011  Redfield et al.
2003/0228306 A1  12/2003  Olson et al.
2013/0216526 A1  8/2013  Olson et al.

FOREIGN PATENT DOCUMENTS

WO    2008/134076 A1    11/2008
WO    WO 2008/134076 A1 *  11/2008
WO    WO 2011/109365 A2 *  3/2011
WO    2011/109365 A2    9/2011

OTHER PUBLICATIONS

Jacobson, J. M., et al., 2010, Anti-HIV-1 activity of weekly or biweekly treatment with subcutaneous PRO 140, a CCR5 monoclonal antibody, J. Infect. Dis. 201(10):1481-1487.*

Jacobson et al., "Anti-HIV-1 Activity of Weekly or Biweekly Treatment with Subcutaneous PRO 140, a CCR5 Monoclonal Antibody." Journal of Infectious Diseases, vol. 201, No. 10, May 15, 2010, pp. 1481-1487.

Castor et al., "The role of chemokines in mediating graft versus host disease: opportunities for novel therapeutics," *Front. Pharm.* 3:1-13, 2012.

Gilliam et al., "Clinical use of CCR5 inhibitors in HIV and beyond," *J. Trans. Med.* 9(Suppl. 1): S9, 2010. (14 pages).

Reshef et al., "Blockade of Lymphocyte Chemotaxis in Visceral Graft-versus-Host Disease," *N. Engl. J Med* 367:135-145, 2012.

Yuan et al., "Prophylaxis of acute graft-versus-host disease by CCR5 blockade combined with cyclosporine A in murine model," *Inflamm. Res.* 64:137-144, 2015.

Jacobson et al. "Phase 2A Study of the CCR5 Monoclonal Antibody PRO 140 Administered Intravenously to HIV-Infected Adults," Antimicrobial Agents and Chemotherapy, Jul. 26, 2010, vol. 54, No. 10, pp. 4137-4142, entire document.

* cited by examiner

*Primary Examiner* — Jeffrey S Parkin
(74) *Attorney, Agent, or Firm* — Seed IP Law Group LLP

(57) ABSTRACT

This invention relates to the use of antibody therapy as a treatment substitute, or for treatment interruption, to treat HIV-1 infected patients. Specifically, the present invention relates to the use of antibody therapy, such as PRO 140 monoclonal anti-body therapy, as a monotherapy for treatment of HIV-1 infected patients.

13 Claims, 16 Drawing Sheets

PRO 140: Mean of the maximum (nadir) $\log_{10}$ reductions in HIV RNA

PRO 140: Mean change from baseline in HIV-1 RNA (Log10 copies/mL) over Time (ITT Subjects)

| | \multicolumn{14}{c|}{Latest Results Date} | | | | | | | | | | | | | |
|---|---|---|---|---|---|---|---|---|---|---|---|---|---|---|
| T# | T1 | T2 | T3 | T4 | T5 | T6 | T7 | T8 | T9 | T10 | T11 | T12 | T13 | T14 |
| Week | -1 | 0 | 1 | 2 | 3 | 4 | 5 | 6 | 7 | 8 | 9 | 10 | 11 | 12 |
| Patient | Date of 1st inject. | 0 VL-1 | 7 VL-2 | 14 VL-3 | 21 VL-4 | 28 VL-5 | 35 VL-6 | 42 VL-7 | 49 VL-8 | 56 VL-9 | 63 VL-10 | 70 VL-11 | 77 VL-12 | 84 VL-13 |
| A | | TND | <40 | TND | <40 | TND | <40 | TND | <40 | 77 | 10660 | | | |
| B | | TND | TND | <40 | 385 | 1891 | 16304 | 35033 | \multicolumn{6}{c|}{VF1-Dual Mixed Tropism} | | | | | |
| C | | <40 | TND | TND | TND | <40 | <40 | <40 | <40 | 79 | <40 | | | |
| D | | TND | TND | TND | TND | TND | TND | TND | <40 | 68 | <40 | | | |
| E | | TND | TND | TND | TND | 138 | 776 | 3311 | \multicolumn{6}{c|}{VF2} | | | | | |
| F | | TND | <40 | 40 | TND | <40 | 40 | <40 | 48 | <40 | | | | |
| G | | TND | <40 | <40 | <40 | 68 | 120 | 331 | 390 | 345 | | | | |
| H | | TND | TND | <40 | TND | <40 | TND | TND | TND | TND | | | | |
| I | | <40 | TND | <40 | 148 | 2074 | 28502 | 6065 | \multicolumn{6}{c|}{VF3} | | | | | |
| J | | TND | TND | TND | 40 | 2769 | 32705 | \multicolumn{7}{c|}{VF4} | | | | | | |
| K | | TND | TND | <40 | <40 | TND | 74 | 13844 | 33849 | \multicolumn{5}{c|}{VF5} | | | | | |
| L | | TND | TND | <40 | <40 | 74 | 367 | 1735 | | | | | | |
| | | | | | | | | | | | | | | |
| Schooley's placebo trial | | 3% | 18% | 43% | 50% | 60% | 75% | 90% | 98% | 100% | | | | |

FIG. 11

SUBSTITUTION MONOTHERAPY TREATMENT FOR HIV-1 INFECTION EMPLOYING ANTIBODY PRO140

RELATED APPLICATIONS

This application claims priority to U.S. provisional patent application Ser. No. 62/039,620, filed Aug. 20, 2014, and U.S. provisional patent application Ser. No. 62/192,941, filed Jul. 15, 2015, the contents of each of the applications are fully incorporated herein by this reference.

TECHNICAL FIELD

This invention relates to the use of antibody therapy as a treatment substitute, or for treatment interruption, to treat HIV-1 infected patients. Specifically, the present invention relates to the use of antibody therapy, such as PRO 140 monoclonal antibody therapy, as a monotherapy for treatment of HIV-1 infected patients.

BACKGROUND

The advent of highly active antiretroviral therapy (HAART) in the mid-1990s resulted in a dramatic increase in survival of HIV patients. HAART is the current standard of care. Due to the substantial progress that has been made over the past two decades in the development of effective and well tolerated combination antiretroviral regimens, most HIV-1 infected persons who initiate antiretroviral therapy at early stages in the disease process and who are fully adherent to their antiretroviral regimens can anticipate life expectancies that are measured in decades. While combination antiretroviral treatment has changed the face of the HIV epidemic and enabled physicians to provide effective therapy, several issues and limitations of these regimens have emerged. Currently, there are over 30 drugs approved for HIV/AIDS treatment, all of them with common problems, including: drug resistance; side effects with long-term morbidities; incomplete recovery of immune function; drug interactions; and requirement for daily, lifelong adherence.

The most significant limitation of continuous therapy (CT) has been the necessity and challenge of continued daily adherence to the medications. It is known that reduced compliance over years of therapy results in drug resistance and subsequent elimination of treatment options.

Further, undesirable metabolic effects are another concern with HIV treatment. There is evidence of increased myocardial infarction rates among patients on antiretroviral therapy. An important study on this subject was the DAD study (Data Collection on Adverse Events of Anti-HIV Drugs), which found an increased risk of coronary artery disease in people on all types of antiretroviral therapy (Law M, Friis-Moller N, Weber R, et al., *Modelling the 3-year risk of myocardial infarction among participants in the Data Collection on Adverse Events of Anti-HIV Drugs (DAD) study*, HIV MED. 2003; 4:1-10). The DAD study also found that some of the risk was lowered upon discontinuation of anti-HIV drugs. Additional metabolic and general side effects of antiretroviral therapy include cardiovascular complications, lipoatrophy, peripheral neuropathy, and accelerated liver disease (Julg B, Goebel F D, *Treatment interruption in HIV therapy: a SMART strategy?*, INFECTION, 2006; 34:186-188 ("Julg")).

Further, the potential risks of CT are generally believed to include higher rates of drug side effects, more difficult adherence (and particularly so for significant patient subsets), and potentially more drug resistance resulting in fewer drug options secondary to higher antiretroviral therapy exposure. The high cost of medications related to CT also continues to be problematic.

The availability of an effective, simplified maintenance regimen would be of benefit to a subset of HIV-1 infected persons who are challenged by adherence and/or chronic nucleoside toxicity.

A number of studies have been conducted to evaluate the possibility of treatment simplification following control of viral replication with an induction regimen. Most of these simplification trials have involved the substitution of a boosted HIV-1 protease inhibitor such as lopinavir or darunavir for an effective combination regimen. Although the strategy has been successful in a substantial fraction of those who undergo regimen simplification, the overall body of evidence suggests that boosted protease inhibitor maintenance therapy is generally less effective than maintenance on a three drug regimen. Factors influencing the likelihood of success include the duration of successful suppression prior to the regimen simplification and the extent to which patients are adherent to their simplified regimens. Although it has also been suggested that some patients may fail because of variability in trough concentrations of protease inhibitors, this has not been substantiated in rigorously conducted studies. Other concerns that have been raised include the ability of HIV-1 protease inhibitors to achieve suppressive levels in the central nervous system. The current consensus appears to be that this approach should be reserved for specific patient populations in which considerations related to chronic nucleoside toxicity and/or adherence to complex antiretroviral regimens are dominant. In these situations, the importance of adherence and of close monitoring of plasma HIV-1 RNA levels has been emphasized. In the case of HIV-1 protease inhibitor maintenance therapy, reestablishment of control of retroviral replication has generally been achieved by resumption of combination therapy.

Thus, there is a need for strategies that can optimize the use of available antiretroviral drugs in order to maximize the benefits while minimizing the risks. Treatment substitution (TS), including intermittent therapy (IT), is one way to attempt to optimize antiretroviral therapy. Two main strategies for IT have been studied: time-defined and CD4+ cell-guided. Time-defined strategies involve predetermined treatment interruption, such as medication breaks on weekends and one-month-on/one-month-off scheduling, in an effort to improve quality of life, promote adherence, decrease antiretroviral exposure, and minimize the development of resistance. The CD4+ cell-guided strategy, used in the National Institutes of Health's Strategies for Management of Antiretroviral Therapy (SMART) study, utilized CD4+ cell counts to determine the starting and stopping point of IT. In other words, antiretroviral treatment is started when the CD4+ cell count falls below a certain threshold, stopped when it increases above a certain level, restarted when the CD4+ cell count again falls below the threshold, and so on.

The potential benefits of TS and IT, including fewer side effects, better adherence, and improved overall health and quality of life, may be weighed against potential risks, including the possible increase in the development of resistance, lasting damage to the immune system, and an increase in the risk of HIV transmission due to non-suppression of viral load.

TS/IT Studies

Based on published data from ACTG5197 trial entitled "A Phase II double-blind, randomized, placebo-controlled study to evaluate the antiretroviral effect of immunization with the MRY Ad5 HIV-1 GAG vaccine in HIV-1 infected individuals who interrupt antiretroviral drug therapy" the viral load will increase within 4 weeks after treatment interruption. See Schooley, Robert T. et al., *ACTG 5197: A Placebo Controlled Trial of Immunization of HIV-1 Infected Persons with a Replication Deficient Ad5 Vaccine Expressing the HIV-1 Core Protein*, J. INFECT. DIS., Sep. 1, 2010, 202(5): 705-716 ("Schooley"). The impact of treatment interruption on the CD4 cell count reduction is also observed after 4 weeks, actually the downward trend in CD4 cell counts can be observed by week 1, as depicted in FIGS. 1-3. This study was conducted in HIV infected men and women of 18 to 55 year old (inclusive), who have maintained viral load suppression for at least 24 months and had a CD4 cell counts of greater than 500 cells/mm3 and HIV-1 RNA<50 copies/mL.

These changes in both viral load and CD4 counts are depicted in FIGS. 1-3. As it is depicted in FIG. 1, if the subjects who have their viral load below 50 copies/mL and their CD4 cell counts>500 cells/mm3 have a treatment interruption, then after 4 weeks approximately 50% of them will have a viral load of >500 copies/mL; and almost 100% of the subjects will have a viral load of >500 copies/mL by 10 weeks. FIG. 2 depicts the actual change in the median viral load and their 95% Confidence Intervals over a period of 16 weeks. After week 3 there is a clear increase in the viral load and by week 6 the viral load reaches the highest level and was maintained through week 16.

As depicted in FIG. 1, in subjects who have CD4 cell count of greater than 500 cells/mm3 and have a treatment interruption, a trend toward a decline in CD4 was observed by week 1. This downward trend in CD4 cell count continued and after 4 weeks of treatment interruption approximately 10%, and by week 16 more than 30%, reduction in their viral load was observed.

Separately, it has been reported that several studies have investigated both CD4+ cell- and time-guided IT strategies (Siegel L, El-Sadr W, New Perspective in HIV Treatment Interruption: The SMART Study, PRN NOTEBOOK, vol. 11, no. 2, October 2006 ("Siegel")). For example, the Staccato trial randomized 430 patients to CT or IT (Ananworanich J, Gayet-Ageron A, Le Braz M, et al., *CD4-guided scheduled treatment interruptions compared to with continuous therapy for patients infected with HIV-1: results of the Staccato randomized trial*, LANCET, 2006; 368:459-465). Patients in the IT group started therapy when their CD4+ counts dropped below 350 cells/mm³ and then stopped therapy once their CD4+ counts increased above 350 cells/mm³. This small study showed 5.8% of the IT patients experienced acute retroviral syndrome. Minor manifestations of HIV infection, such as candidiasis and thrombocytopenia, were more common in the IT group, while adverse events, including diarrhea and neuropathy, were more common in the CT group. Ten patients (2.3%) had resistance mutations; there were no differences between groups. There was a 62% savings in antiretroviral therapy costs (Julg).

Additionally, it has been reported that the Window-ANRS 106 trial randomly assigned 403 patients with undetectable viral loads and CD4+ counts greater than or equal to 450 cells/mm³ while on antiretroviral therapy to receive either CT or IT in eight-week off/on cycles. The primary endpoint of CD4+ counts less than 300 cells/mm³ was reached by 3.6% in the IT group, compared with 1.5% in the CT group. At week 96, the proportion of patients with CD4+ counts greater than 450 cells/mm³ and viral loads of 400 copies/mL or less was 75% vs. 92% and 81% vs. 90%, IT or CT, respectively. The IT arm, the investigators concluded, appeared safe and without excess resistance, while reducing antiretroviral exposure by 48.5%.

It has been reported that another study, the ANRS 1269 Trivican trial, randomized 326 patients on antiretrovirals therapy with CD4+ counts greater than 350 cells/mm³ and undetectable viral loads to CT or one of two IT strategies: CD4+ cell-count-guided (stopping at 350 cell/mm³ and restarting at 250 cells/mm³) or time-guided (two-months-off, four-months-on). At an interim point, the CD4+ cell-guided arm was terminated prematurely due to safety concerns. The results demonstrated a two-fold higher serious morbidity rate in the CD4+ cell-guided group, compared with the CT group, with recommendations for future studies to utilize higher CD4 count thresholds.

In yet another study, the ISS PART trial, it has been reported 273 subjects were randomized to one of five different time-guided IT schedules (one to three months off therapy, followed by three months on treatment) or CT, with the primary endpoint being the proportion of patients with CD4+ counts greater than 500 cells/mm³ after 24 months. Significantly more patients in the CT group reached the primary endpoint (86.5% vs. 69.1%; P=0.0075), with similar rates of virological failure.

In connection with the SMART study, results of a two-armed treatment comparison of CT to CD4+ cell-guided IT have also been reported. The goal of the CT arm was to use antiretroviral therapy, irrespective of the CD4+ cell count, to achieve and maintain undetectable viral loads. The goal of the IT arm was to defer therapy until the CD4+ count was below 250 cells/mm³, continue treatment until the CD4+ count increased above 350 cells/mm³, with subsequent stops and restarts using these CD4+ cell count cutoffs. Patients entering the SMART study were required to have a current CD4 count of greater than 350 cells/mm³ (CD4+ count nadir was permitted to be lower). They were randomized 1:1, in an open-label fashion, to either CT or IT. The SMART investigators hoped to enroll 6,000 patients and to accumulate approximately eight years of follow-up data. The primary endpoints were progression to AIDS or death, survival, serious complications (e.g., cardiovascular, renal, and hepatic), serious disease progression events (e.g., disseminated MAC, toxoplasmosis, cryptococcosis, Kaposi's sarcoma), and grade 4 events. Additional comparisons involved adherence, side effects, metabolic complications, quality of life, drug resistance, and cost.

It has been reported that the SMART study was halted on Jan. 11, 2006, due to safety concerns. At that time, 5,472 patients were enrolled and included in an intent-to-treat analysis. In an effort to obtain a comprehensive understanding of the primary outcome, several sub-studies were conducted to assess various outcome measures, including quality of life, risk behavior, body composition and metabolic parameters, neurological complications, and anal dysplasia. The SMART study represents an international effort with participants from 33 countries and 318 sites. The majority of the participants were from North America and the United States with additional participation through sites in Europe, Africa, Asia, and South America. Baseline characteristics of the SMART study groups include a median age of 46 years: 27% were women and 30% were black. The median follow-up time was 14 months, with 2% lost to follow up. The median CD4+ count at entry was approximately 598 cells/mm³, with median nadirs of approximately 251 cells/mm³.

Seventy-one percent had viral loads less than 400 copies/mL, 24% had prior clinical AIDS, and 4.7% were antiretroviral naïve.

Reported results of the SMART study demonstrate statistically significant differences in clinical disease progression including death between the two groups. There were 117 events per 100 person-years of follow up in the IT group, compared with 47 events per 100 person-years of follow up in the CT group. This translated into a relative risk of clinical disease progression of 2.5 for the IT arm (P<0.0001). Kaplan-Meier curves demonstrated slow and consistent accumulation of events in both arms over time, but with the IT group showing higher event rates starting four months after randomization. The component breakdown of the primary SMART study endpoint shows that the relative risk favors the CT group with respect to survival and disease progression. Notably, despite greater exposure to antiretroviral therapy, severe cardiovascular, hepatic, and renal complications were unexpectedly lower in the CT group, with a cumulative relative risk of 1.5. When the primary endpoint of HIV disease progression or death was further subdivided by race and sex, the CT group still maintained a clear advantage over the IT arm. The SMART study investigators also subdivided the outcomes by baseline CD4+ cell counts and viral loads, and demonstrated the same advantage to the viral suppression (CT) arm. There were particular safety concerns regarding the group of patients with low CD4+ nadirs. However, the data demonstrated that these patients were no more likely to experience disease progression or death when compared with patients with higher CD4+ nadirs. In fact, all groups of CD4+ nadirs favored the CT group equally. With respect to viral loads at study entry, patients with viral loads less than 400 copies/mL had many more events in the IT arm, while those with detectable HIV-RNA levels did equally well in both arms.

Reports of the SMART study results showed that IT compared with CT, was associated with increased risks of HIV disease progression or death, serious HIV disease progression, and severe complications, and that the results were not affected by gender, race, baseline CD4+ cell count, or nadir CD4+ cell count. Moreover, the risk was determined to be three-fold higher for patients on antiretroviral therapy with baseline viral loads below 400 copies/mL. Based on the SMART study, and other IT studies, it has been conventionally accepted that episodic use of antiretroviral therapy based on CD4+ cell counts, as utilized in the SMART study design, is inferior to continuous antiretroviral therapy for the management of antiretroviral-experienced patients. Further, in contrast to other IT studies that measured only viral load and CD4+ counts, the SMART study is conventionally considered particularly powerful because a broad range of clinical endpoints were examined. In sum, the reported results of SMART study are conventionally believed to discourage IT.

Although PRO 140 would require either subcutaneous (SC) or intravenous (IV) administration, its favorable pharmacokinetics might allow dosing as infrequent as once or twice monthly. The ability to administer the drug infrequently under medical supervision could obviate one of the continuing challenges of close adherence to daily boosted protease inhibitor regimens that appear to be relatively unforgiving in maintenance settings when administered as the sole antiretroviral regimen. This is an open-label pilot study of PRO 140 monotherapy as maintenance therapy for those previously fully suppressed on combination antiretroviral regimens.

HIV-1

Infection of cells by human immunodeficiency virus type I (HIV-1) is mediated by the viral envelope (Env) glycoproteins gp120 and gp41, which are expressed as a noncovalent, oligomeric complex on the surface of virus and virally infected cells. Entry of the virus into target cells proceeds through a cascade of events at the cell surface that include (1) binding of the viral surface glycoprotein gp120 to a cell surface receptor, (2) Env binding to fusion coreceptors, and (3) multiple conformational changes in gp41.

The first high-affinity interaction between the virion and the cell surface is the binding of gp120 to cell surface CD4, which is the primary receptor for HIV-1. This binding induces conformational changes in gp120, which enable it to interact with one of several chemokine receptors. The CC-chemokine receptor 5 (CCR5) is the major co-receptor for macrophage-tropic (R5) strains, and plays a crucial role in the transmission of HIV-1. T cell line-tropic (X4) viruses use CXCR4 to enter target cells, and usually, but not always, emerge late in disease progression or as a consequence of virus propagation in tissue culture. Some primary HIV-1 isolates are dual-tropic (R5X4) since they can use both co-receptors, though not always with the same efficiency. Binding of gp120 to a chemokine receptor in turn triggers conformational changes in the viral transmembrane glycoprotein gp41, which mediates fusion of the viral and cellular membranes. Each stage of this multi-step process can be blocked with inhibitors of the appropriate viral or cellular protein, and the inhibitors of gp120, gp41, CD4 and coreceptor are collectively known as entry inhibitors. Entry inhibitors represent at least 4 distinct classes of agents based on their molecular targets and determinants of viral resistance.

CCR5 as a Target for Anti-HIV-1 Therapy

As first demonstrated in 1986, HIV-1 binds to target cells via the CD4 receptor but requires additional host cell factors to mediate entry. Over the next decade, a number of candidate coreceptors were proposed, but none reproducibly mediated viral entry when coexpressed with CD4 in otherwise nonpermissive cells. However, in 1996, certain chemokine receptors, mainly CCR5 and CXCR4, were shown to serve as requisite fusion coreceptors for HIV-1.

A link between HIV-1 and chemokines are small (about 8 kDa) homologous soluble proteins. Chemokines mediate the recruitment and activation of immune cells. They are classified as CC-, CXC-, $CX_3C$- and XC-chemokines based on the number and sequential relationship of the first two of four conserved cysteine residues; most are either CC- or CXC-chemokines. The CC-chemokines RANTES, MIP-1α and MIP-1β, were shown to block replication of primary macrophage-tropic strains of HIV-1. Using expression cloning techniques, It was discovered that the chemokine receptor fusin (later renamed CXCR4) was a fusion coreceptor for strains of HIV-1 adapted to growth on T cell lines. Shortly thereafter, several groups reported the cloning of CCR5, a CC chemokine receptor with specificity for RANTES, MIP-1α and MIP-1β, and others then demonstrated that CCR5 was the main entry cofactor used by primary macrophage-tropic HIV-1 isolates. The patterns of CCR5 and CXCR4 expression helped solve long-standing riddles concerning the tropism of different strains of HIV-1. Macrophage-tropic, T-cell-line-tropic and dual-tropic viruses could be more descriptively classified as being R5, X4 and R5X4 viruses based on their abilities to utilize CCR5, CXCR4 or both receptors, respectively, for entry.

A variety of other chemokine receptors can function as HIV-1 coreceptors when over-expressed in vitro. The list includes CCR8, Apj, V28, US28, CCR2b, CCR3, gpr1, Bonzo (STRL33, TYMSTR), and BOB (gpr15). Clearly, proteins belonging to the chemokine receptor family have biochemical properties that promote HIV-1 membrane fusion. However, most of the above-mentioned coreceptors are not very efficient, are not normally coexpressed with CD4, and function only with certain strains of HIV-1, HIV-2 or SIV. The in vivo relevance of these alternative coreceptors has not been established.

Several factors make CCR5 an attractive target for new antiretroviral therapies. CCR5 plays a central role in HIV-1 transmission and pathogenesis, and naturally-occurring mutations in CCR5 confer protection from HIV-1 infection and disease progression. The most notable CCR5 polymorphism involves a 32 bp deletion in the coding region of CCR5 (A32). The A32 allele encodes a nonfunctional receptor that fails to reach the cell surface. Individuals who possess one normal and one mutant CCR5 gene express lower levels of CCR5, and their T cells are less susceptible to R5 virus infection in vitro. A32 heterozygotes experience a milder course of disease characterized by reduced viral burdens and delayed progression to AIDS. These results support the concept that reducing CCR5 availability can lower viral replication and slow disease progression.

Individuals with two mutant CCR5 genes comprise a significant fraction of people of northern European descent; the demography is suggestive of a prior pandemic of a CCR5-using pathogen. Such individuals represent human CCR5 "knockouts" in that they do not express a functional CCR5 protein. Except in rare instances, these individuals are resistant to HIV-1 infection, and their T cells cannot be infected with R5 viruses in vitro. These findings underscore the central role of CCR5 in HIV-1 transmission. In fact, it is now known that R5 viruses mediate transmission in nearly all cases and mediate progression to AIDS in most cases.

Importantly, individuals who lack CCR5 enjoy normal health and display no obvious immunologic or other defects. This may reflect the redundancy of chemokine signaling pathways and the rather limited pattern of expression of CCR5. CCR5 expression is largely confined to activated T cells and macrophages, which represent the primary targets for HIV-1 infection in vivo, although low-level CCR5 expression has been reported on other tissues, such as smooth muscle.

CCR5 knockout mice have been generated and provide further insight into the effects of abrogating CCR5 function. CCR5 knockout mice develop normally and are ostensibly healthy, although minor alterations in immune responses can be observed upon challenge with particular pathogens. In contrast, the CXCR4 knockout is a lethal phenotype in mice, and has not been observed in humans.

Taken together, these genetic analyses strongly support a new therapeutic approach based on CCR5 as a drug target. The error-prone nature of reverse transcriptase generates immense genetic diversity that fosters the development of drug-resistant isolates, and HIV-1's ability to utilize multiple fusion coreceptors provides one path to resistance. Drug-resistant viruses have been isolated for all marketed antiretrovirals, which nevertheless provide important therapeutic benefit when used in appropriate combinations. Thus, despite the potential emergence of drug-resistant viruses, CCR5-targeting agents may serve as a new treatment paradigm for HIV-1 infection.

Although the apparent non-essential nature of CCR5 suggests that CCR5 antagonists may be well tolerated in vivo, further studies are required to determine that long-term effects of abrogating CCR5 function in individuals whose immune systems developed in its presence. Such potentially deleterious effects may be mitigated by use of agents that bind to CCR5 and inhibit binding of HIV-1 thereto, but do not impair normal CCR5 function. One agent demonstrated to have such properties is the humanized anti-CCR5 mAb, PRO 140, which effectively blocks HIV-1 replication at concentrations that do not inhibit the physiologic activity of CCR5. PRO 140 was identified using a fluorescence resonance energy transfer (RET) assay screen for anti-HIV activity. It is potently antiviral, having an $IC_{90}$ of about 4 μg/ml and protects diverse primary target cell types. Repeated administration of PRO 140 led to prolonged control of HIV-1 replication without viral escape in the hu-PBL SCID mouse model.

Subsequent to the identification of the small-molecule CCR5 antagonist, TAK-779, several other small-molecule CCR5 antagonists have been identified. Four of these (SCH-C, SCH-D, UK-427,857, GW873140) have completed similarly designed Phase 1 studies in HIV-infected individuals. Each of these agents mediated dose-dependent about 1 $log_{10}$ mean reductions in HIV-1 RNA levels during the treatment period of 10-14 days. As expected, viral loads rebounded to baseline levels following cessation of therapy. The most common drug-related side-effects were neurologic (headache, dizziness) and gastrointestinal (nausea, diarrhea, flatulence), and these were not dose limiting. With the exception of SCH-C, none of the above-identified agents induced clinically significant changes in QTc intervals.

A double-blind, placebo-controlled, single oral dose study has also been conducted to evaluate the safety, tolerability, and pharmacokinetics of TAK-652, the successor compound to TAK-779, in healthy male volunteers. The single administration of TAK-652 solution was reportedly safe and well tolerated.

Overall, these studies provide preliminary validation of CCR5 as a target for HIV-1 therapy. While the small-molecule CCR5 antagonists represent patentably distinct chemical series with differing pharmacokinetic and metabolic properties, the compounds share many properties in their inhibition of CCR5 function, binding site on CCR5, resistance profiles, and dosing regimen. These similarities may conceivably limit the number of genuine treatment options afforded by small-molecule CCR5 antagonists. Moreover, it remains to be determined whether there are untoward consequences of chronic blockade of CCR5 function, and the utility of small-molecule CCR5 antagonists for HIV-1 therapy remains to be established by demonstration of appropriate safety and efficacy in Phase 3 clinical studies.

Monoclonal Antibody Therapeutics

In recent years, mAb products have provided new standards of care in diverse disease settings. Currently, several mAbs are approved by the U.S. Food and Drug Administration (FDA) for indications including cancer, autoimmune disease, transplant rejection and viral infection. In many instances, mAbs provide safety, efficacy and ease-of-use profiles that are unrivalled by small-molecule compounds.

The humanized anti-CCR5 mAb, PRO 140, is structurally, functionally and mechanistically distinct from the small-molecule CCR5 antagonists and therefore represents a unique CCR5 inhibitor class. PRO 140 is a humanized version of the murine mAb, PA14, which was generated against $CD4^+$ $CCR5^+$ cells. PRO 140 binds to CCR5 expressed on the surface of a cell, and potently inhibits HIV-1 entry and replication at concentrations that do not affect CCR5 chemokine receptor activity in vitro and in the hu-PBL-SCID mouse model of HIV-1 infection.

Important differences between PRO 140 and small-molecule CCR5 antagonists are summarized in Table 1. It is evident from Table 1 that, whereas small-molecule CCR5 antagonists in development share many properties, PRO 140 is clearly distinct from these small-molecule inhibitors. The differences between the two CCR5 inhibitor classes reveal that PRO 140 may offer a fundamentally distinct, and in many ways complementary, product profile from that of small-molecule CCR5 antagonists. Indeed, PRO 140 represents a novel therapeutic approach to treating HIV-1 infection and could play an important role in HIV-1 therapy irrespective of small-molecule CCR5 antagonists.

TABLE 1

Comparison of PRO 140 and small-molecule CCR5 antagonists

|  | Small Molecules | PRO 140 |
|---|---|---|
| Identification Screen | Chemokine Binding | HIV-1 Entry |
| Block Natural Activity of CCR5 | Yes | No |
| Potential for Immune Suppression/Dysregulation | Yes | No |
| Tolerability | Cardiac, Neurological Toxicities for some | No Toxicity |
| Binding site on CCR5 | Common Hydrophobic Pocket defined by Transmembrane Regions of CCR5 | Extracellular Epitope that spans Multiple Hydrophilic Domains |
| Viral Cross-Resistance | Significant | Limited |
| Development of Resistance in Vitro | 6 to 19 weeks | None at 40 weeks |
| Drug-Drug Interactions | Significant | Unlikely |
| Food Interactions | Significant | Unlikely |
| Dosing | Once or Twice Daily | Biweekly to Monthly |

PRO 140 is a humanized IgG4,κ monoclonal antibody (mAb) to the C-C chemokine receptor type 5 (CCR5), under development as therapy for human immunodeficiency virus (HIV) infection. PRO 140 is directed at an ECL2 domain of the CCR5 cell surface receptor for HIV-1. Binding of this domain of the CCL5 molecule interferes with viral entry by interfering with the final phase of viral binding to the cell surface prior to fusion of the viral and cell membranes. Thus, PRO 140 is a viral-entry inhibitor and belongs to a new class of HIV/AIDS therapeutics that are intended to protect healthy cells from viral infection. PRO 140 is a humanized monoclonal antibody directed against CCR5, a molecular portal that HIV uses to enter cells. Prior to the current TS studies, PRO 140 was the subject of four Phase 1/1b and two Phase 2a clinical trials, each of which demonstrated its ability to significantly reduce HIV viral load in human test subjects infected with HIV. The clinical studies demonstrate that PRO 140 effectively blocks the HIV co-receptor CCR5, and clinical trial results thus far indicate that it does not affect the normal cell function. That is, PRO 140 1) stops HIV replication without blocking immune function, 2) provides prolonged antiviral activity and tolerability, 3) has a different resistance profile compare to any HIV drugs, 4) has no toxicity (unlike all of today's HIV drugs), and 5) is designated as a FDA Fast Track drug candidate. The Phase 1 and 2a Clinical Results (based on data from over 110 patients) shows that PRO 140 provides for rapid viral load suppression better than or as good as any HIV Drug in the market today with one injection. See FIG. 2.

Nucleic acids encoding heavy and light chains of the humanized PRO 140 antibody have been deposited with the ATCC. Specifically, the plasmids designated pVK-HuPRO 140, pVg4-HuPRO140 (mut B+D+I) and pVg4-HuPRO140 HG2, respectively, were deposited pursuant to, and in satisfaction of, the requirements of the Budapest Treaty with the ATCC, Manassas, Va., U.S.A. 20108, on Feb. 22, 2002, under ATCC Accession Nos. PTA 4097, PTA 4099 and PTA 4098, respectively. The American Type Culture Collection (ATCC) is now located at 10801 University Boulevard, Manassas, Va. 20110-2209.

PRO-140 has been administered intravenously or subcutaneously to HIV-1 infected individuals in Phase 1 and Phase 2 studies of safety, tolerability, pharmacokinetics and pharmacodynamics. The drug has been well tolerated following administration of single doses of 0.5 to 5 mg/kg or up to three weekly doses of up to 324 mg. Single subcutaneous doses of 324 mg have resulted in drops in plasma HIV-1 RNA levels of approximately 1.0 $\log_{10}$. Repetitive weekly administration of this dose of PRO 140 has been associated with drops in plasma HIV-1 RNA levels of approximately 1.5 $\log_{10}$. Serum concentrations of PRO 140 above the $IC_{50}$ for clinical isolates of HIV-1 are maintained for at least 2 weeks following a single dose of 324 mg. Plasma HIV-1 RNA levels rise to baseline levels as PRO 140 is cleared from the plasma and, presumably, other compartments.

The applicant submits that the PRO 140 IgG4 antibody is superior to all of today's HIV therapies in that it has far fewer side effects, much less toxicity, leads to much better patient adherence, and achieves a better viral load drop upon initial administration than any other HIV drug. Thus, the PRO 140 antibody appears to be a powerful antiviral agent leading to potentially fewer side effects and less frequent dosing requirements as compared to daily drug therapies currently in use.

FIGURES

FIG. 1 relates to a prior art Schooley study by detailing the decrease in CD4 cell count for HIV-infected patients taken off their standard treatment regimen.

FIG. 2 relates to the same prior art Schooley study and shows the viral rebound kinetics following interruption of antiretroviral therapy for HIV-infected patients FIG. 3 provides historical data Kaplan-Meier estimates from the time to HIV-1 RNA>500 copies/mL.

FIG. 4 provides the mean of maximum (nadir) $\log_{10}$ reductions in HIV RNA and compares placebo, with 0.5 mg/kg, 2 mg/kg, and 5 mg/kg dosages.

FIG. 5 provides the mean $\log_{10}$ reductions in HIV RNA over time.

FIG. 6 provides PRO 140 serum concentrations following a single intravenous injection in HIV-infected individuals, and shows differences between 0.5 mg/kg (represented by a square), 2 mg/kg (represented by a triangle, and 5 mg/kg (represented by a diamond) amounts.

FIG. 7 provides mean change from baseline in HIV-1 RNA ($Log_{10}$ copies/mL) over time (ITT Subjects), and shows the differences between placebo (represented by a diamond), 5 mg/kg (represented by a square), and 10 mg/kg (represented by a triangle) amounts.

FIGS. 8A and 8B. FIG. 8A provides data regarding the mean change from baseline in HIV-1 RNA ($Log_{10}$ copies/mL) over time (ITT Subjects) and the use of PRO 140 as monotherapy, administered either weekly or biweekly. FIG. 8A shows the differences between placebo (line without shaped marker), 162 mg weekly (line with square marker), 324 mg weekly (line with circle), and 324 biweekly (line with triangle). FIG. 8B provides the mean of the maximum (nadir) $\log_{10}$ reductions in HIV RNA for the same study reflected by FIG. 8A.

FIG. 9 is an alternate version of FIG. 8A and provides data regarding the mean change from baseline in HIV-1 RNA (Log$_{10}$ copies/mL) over time (ITT Subjects) and the use of PRO 140 as monotherapy, administered either weekly or biweekly. FIG. 9 shows the differences between placebo (line without shaped marker), 162 mg weekly (line with square marker), 324 mg weekly (line with circle), and 324 biweekly (line with triangle) and fills in the areas provided for each of these dosage regimes to emphasize the differences in effects.

FIGS. 10A, 10B, 10C, and 10D provide the change in CD4+ cell counts in subjects treated with subcutaneous PR0140. FIG. 10A shows the effects of placebo. FIG. 10B shows the effects of 162 mg dosed weekly, on days 1, 8, and 15. FIG. 10C shows the effects of 324 mg dosed biweekly, on days 1 and 15, with placebo administered on day 8). FIG. 10D shows the effects of 324 mg dosed weekly, on days 1, 8, and 15.

FIG. 11 provides interim study results. After four weeks of PRO 140 monotherapy, no patient experienced virologic failure. Half the patients maintained suppressed viral loads after 8 weeks of monotherapy. Five patients, however, experienced virologic failures.

DETAILED DESCRIPTION

The present inventors have achieved positive results from a TS study and an extended TS study in patients with HIV. The first TS study was designed to evaluate the efficacy, safety, and tolerability of PRO 140 monotherapy for the maintenance of viral suppression in patients who were stable on combination antiretroviral (ART) therapy in 40 subjects. Subjects were shifted from daily oral antiretroviral regimen to PRO 140 monotherapy (weekly SC injection) for up to 12 weeks. Those subjects from the first TS study who were able to maintain viral suppression were allowed to continue PRO 140 monotherapy for up to an additional 60 weeks under the Extension study.

Figure 1:
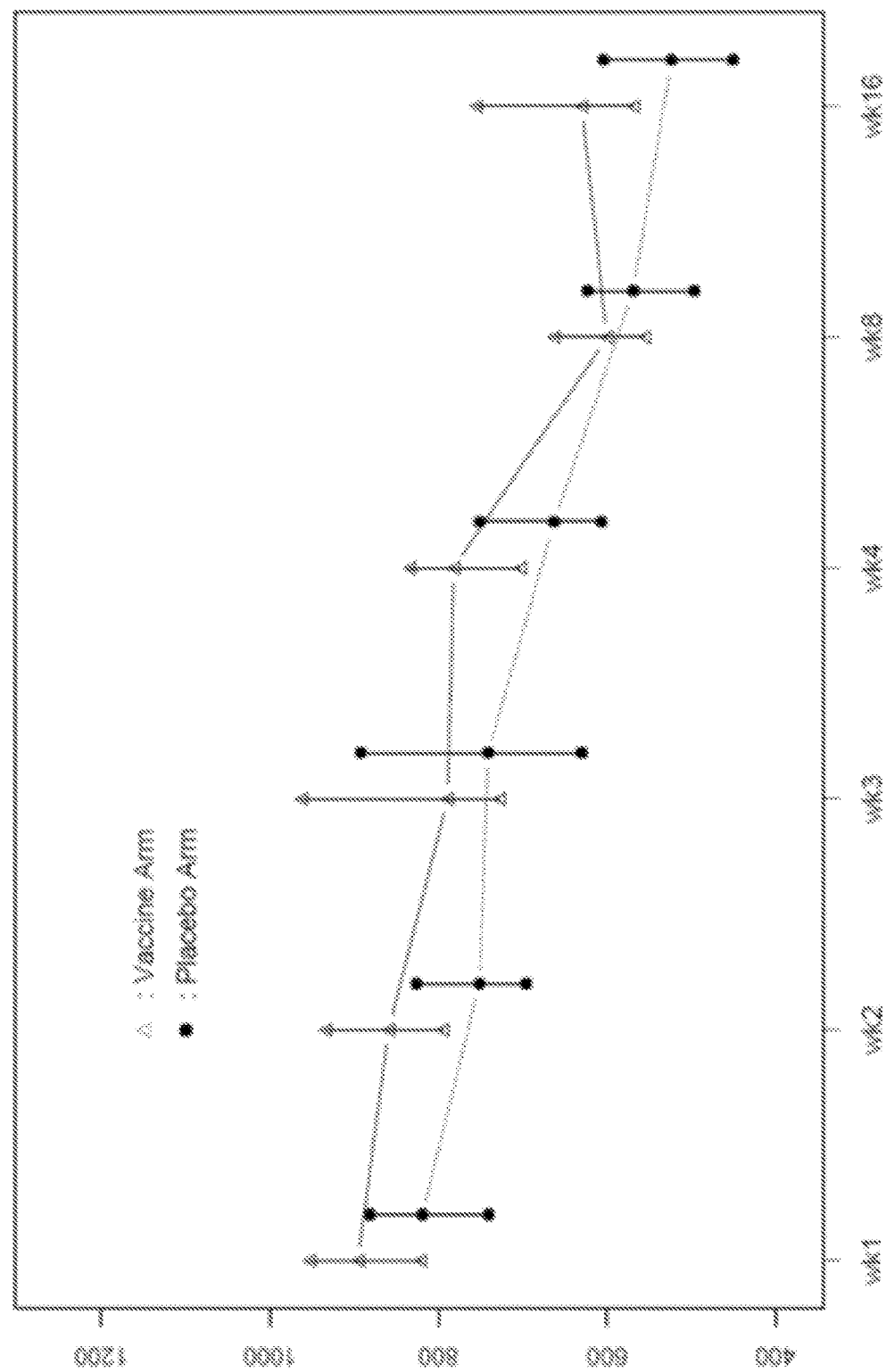
Figure 2:
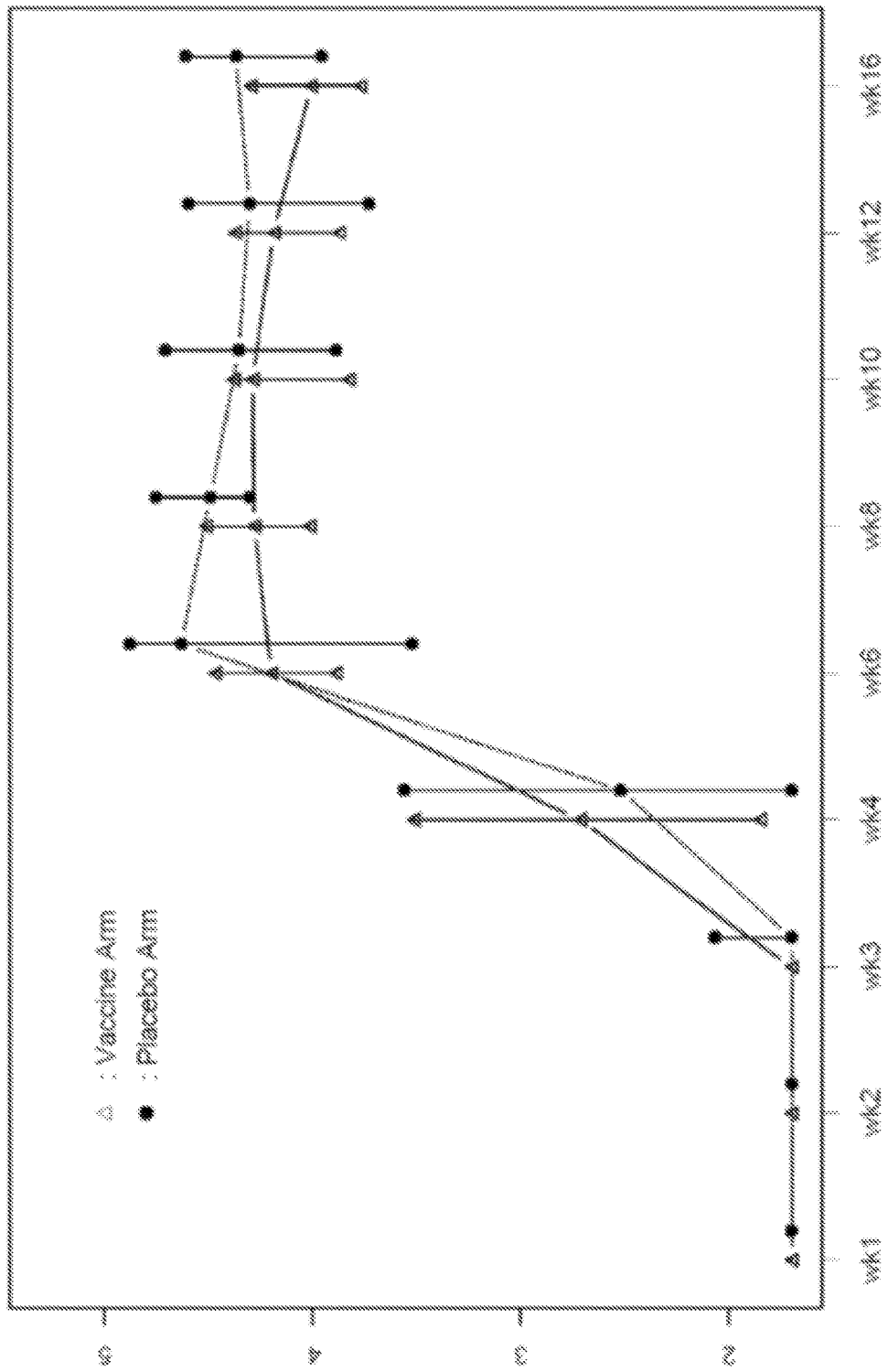
Figure 3:
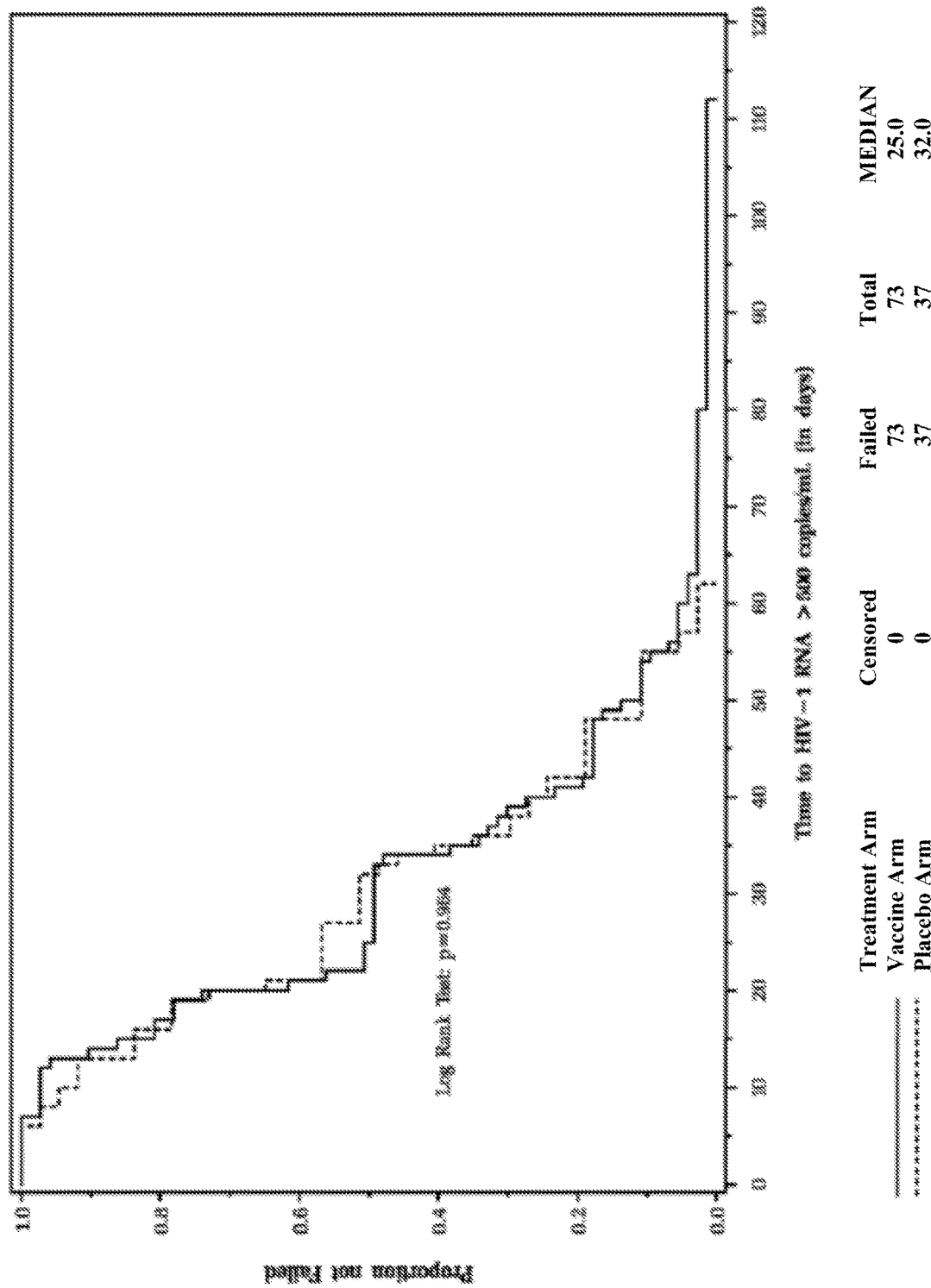
Figure 4:
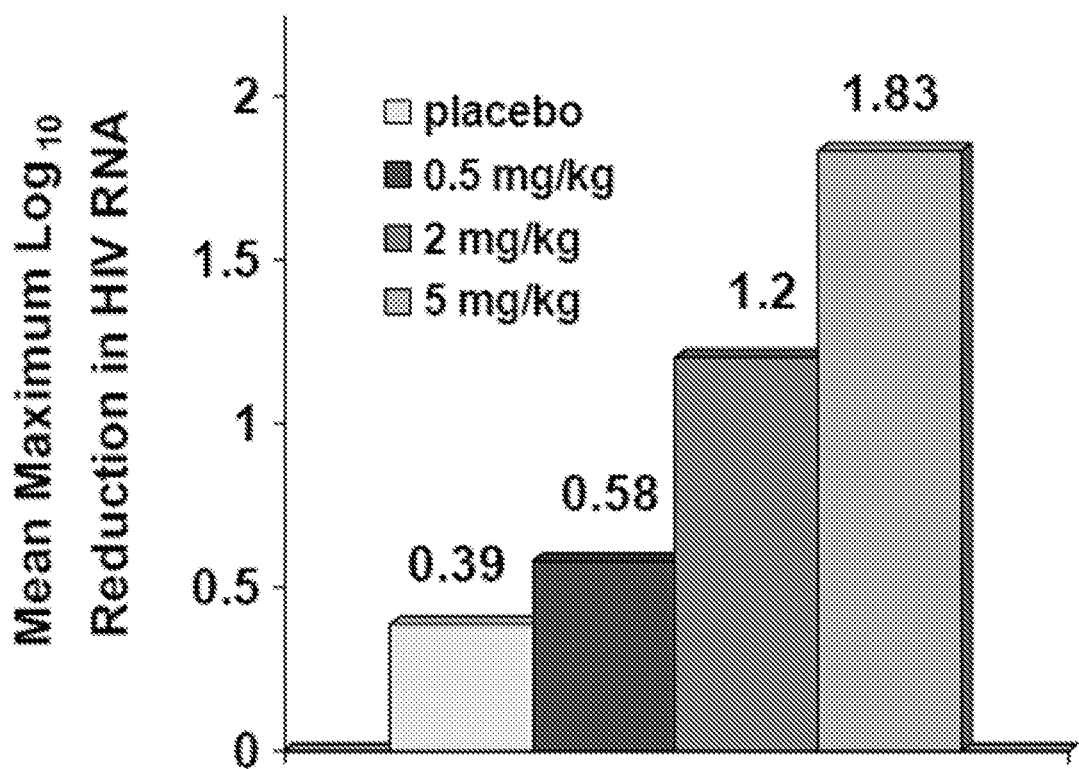
Figure 5:
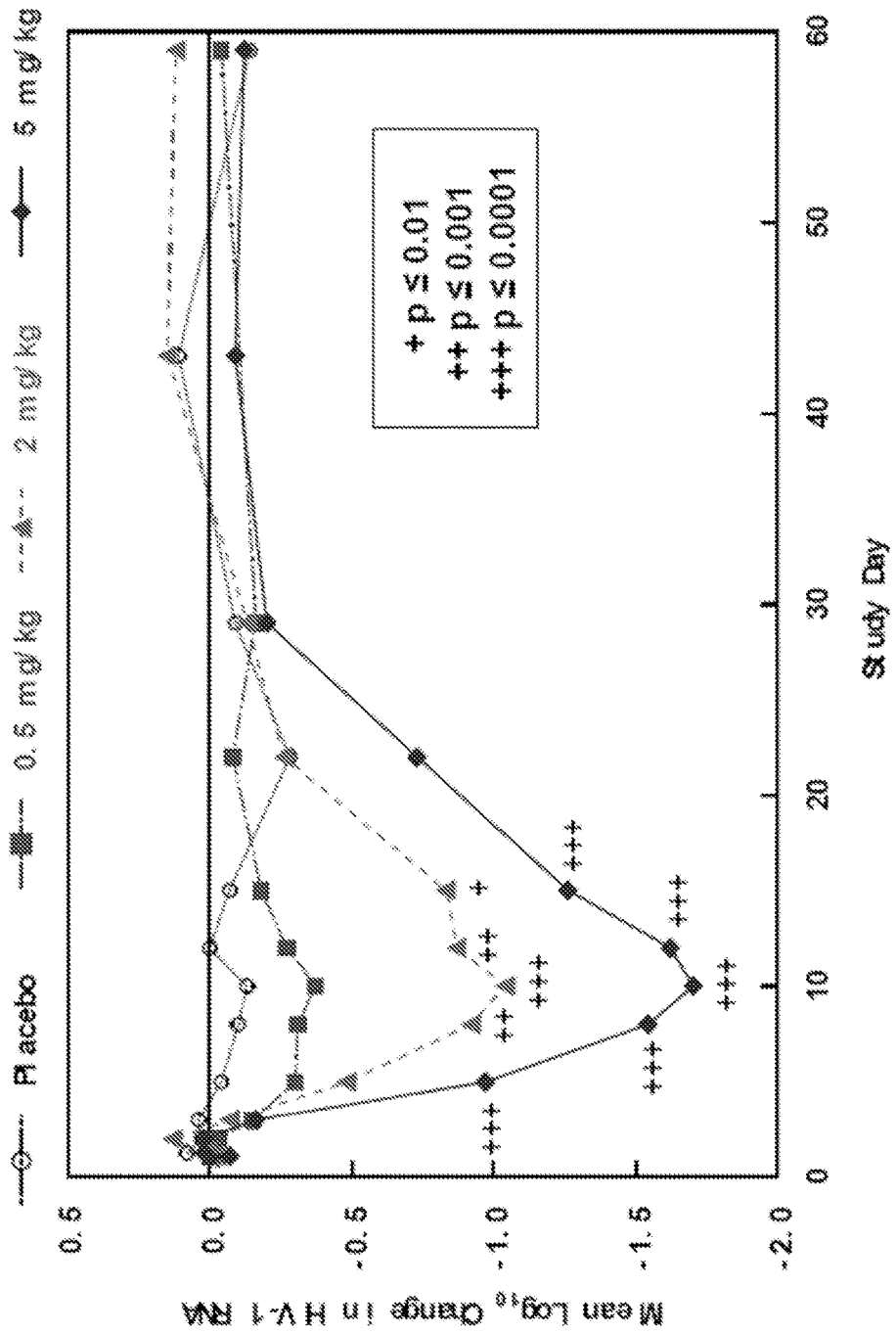
Figure 6:
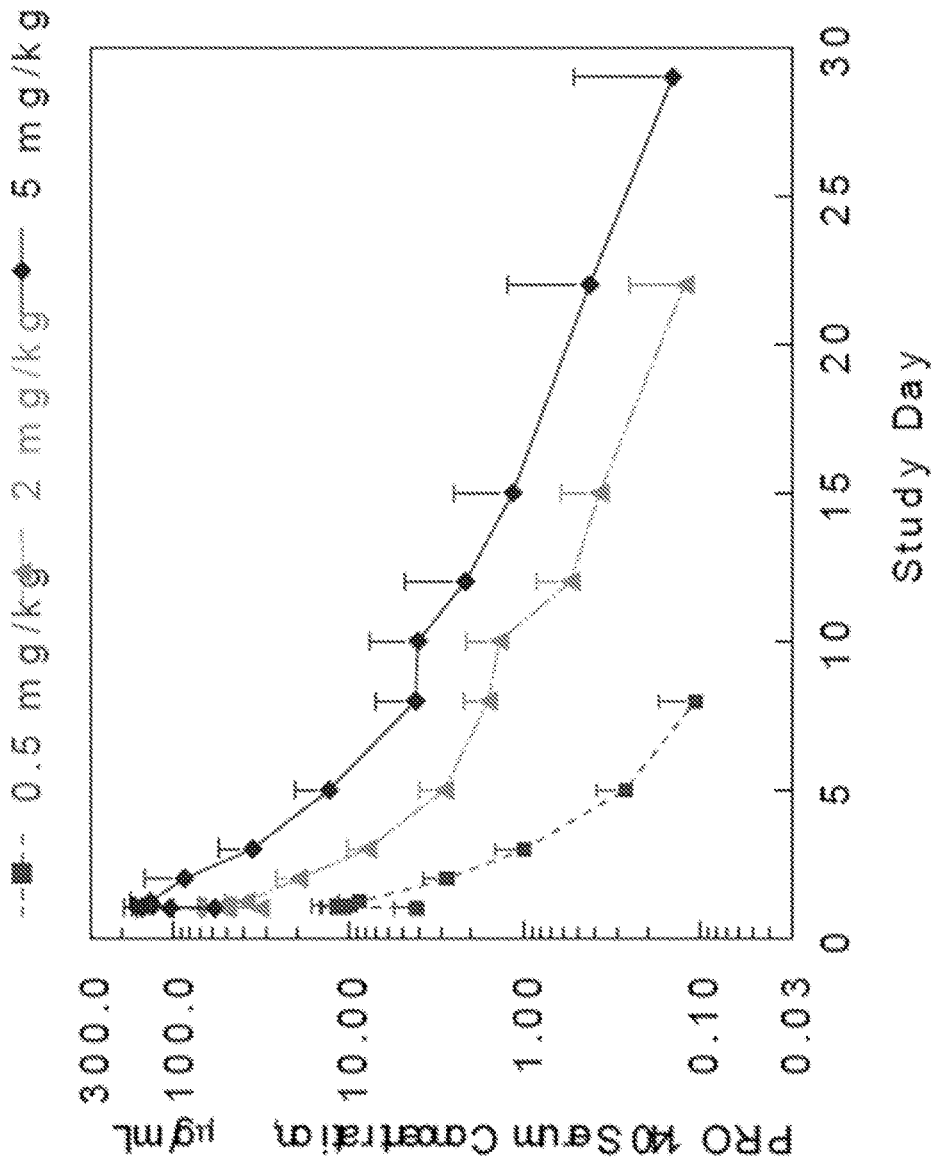

Studies for PRO 140, and its use for treatment substitution purposes, build upon several prior studies, some of which have been disclosed in earlier publications and patent applications to varying degrees. These prior studies include an initial proof of concept study was a randomized, double-blind, placebo-controlled study in subjects with early-stage, asymptomatic HIV infection, only R5 HIV-1 detectable, and no antiretroviral therapy for 12 weeks. Subjects (n=39) were randomized to receive a single IV injection of placebo or PRO 140 at doses of 0.5, 2, or 5 mg/kg. Subjects were monitored for antiviral effects, safety and PRO 140 pharmacokinetics (PK) for 58 days. The study enrolled 31 males and 8 females. The median age, CD4+ cell count and HIV-1 RNA at baseline were 40.3 years, 484 cells/µL and 26,900 copies/mL, respectively. The baseline characteristics were similar for the different treatment groups. PRO 140 demonstrated potent, rapid, prolonged and dose-dependent antiviral activity (FIG. 4 and FIG. 5). A single 5 mg/kg dose reduced viral loads by 1.83 log$_{in}$ on average (FIG. 6). These reductions represent the largest antiviral effects reported after just one dose of any HIV-1 drug [Jacobson J M, 2008].

In the 5 mg/kg group, mean viral load reductions of greater than 1 log$_{in}$ were sustained for 2-3 weeks post-treatment (FIG. 6).

There was no change in R5 virus susceptibility to PRO 140 following treatment. All subjects had R5-only virus at screening in the first-generation TROFILE® assay. R5-only tropism results were observed in all subjects at all other time points, with two exceptions: One of nine (11%) of placebo subjects had dual/mixed virus at baseline and all subsequent time points, reflecting a spontaneous and stable switch in co-receptor tropism results. One of 30 (3%, 0.5 mg/kg group) had a dual/mixed tropism result on day 8 and R5-only results at all other time points, including the end of the day. Clonal analysis of the dual/mixed virus revealed that it reflected outgrowth of pre-existing undetected virus rather than mutation of an R5 virus to a dual/mixed virus following treatment. Therefore, no significant development of viral resistance to PRO 140 was observed despite potent and prolonged (2-3 weeks on average) viral suppression, followed by slow washout of the drug. Given that resistance to other classes of HIV-1 drugs can develop within one week of monotherapy, the findings indicate that PRO 140 presents a high barrier to viral resistance in vivo.

FIG. 6 illustrates the mean serum concentrations of PRO 140 after IV injection. Serum levels increased with increasing dose. The mean Area Under Curve (AUC) from time zero to infinity (AUC∞) values were 11.1, 74.3 and 278 mg×day/L for the 0.5, 2 and 5 mg/kg groups. The mean serum half-life was 3.5-3.9 days in the two highest dose groups. In addition, PRO 140 significantly masked CCR5 on circulating lymphocytes for 2-4 weeks. The PK and receptor occupancy data were broadly consistent with the duration of antiviral effects. FIG. 6 illustrates the mean serum concentrations over time by treatment group. The error bars depict standard deviations. The mean serum half-lives were 3.9 days and 3.5 days in the 2 mg/kg and 5 mg/kg dose groups, respectively.

Intravenous PRO 140 was generally well tolerated. No drug-related serious events or dose limiting toxicity was observed. The most common adverse events (headache, lymphadenopathy, diarrhea, and fatigue) were observed at similar frequencies across the placebo and PRO 140 dose groups. There was no significant effect on QTc interval intervals or other electrocardiographic parameters, and there were no remarkably laboratory findings. There was no loss or depletion of CD4+ or CCR5+ cells from the circulation. At the 5 mg/kg dose, there was a trend towards increased CD4+ cell counts from baseline, with mean changes of +129, +96 and +83 cells/µL observed on days 8, 15, and 22, respectively.

Another prior study for PRO 140 2301 was a multi-center, randomized, double-blind, placebo-controlled, parallel group study in 30 male and female adult subjects infected with HIV-1. Subjects were randomized to one of three groups (N=10/group), each receiving one of three treatments: (i) a single IV dose of 5 mg/kg by 30-minute IV infusion; (ii) a single IV dose of 10 mg/kg by 30-minute IV infusion; (iii) a single placebo dose by 30-minute IV infusion. The objective of the study was to assess and characterize the PK and PD of PRO 140 administered by IV infusion, assess efficacy at a new dosage level, and safety and tolerability of single doses of PRO 140.

Figure 7:
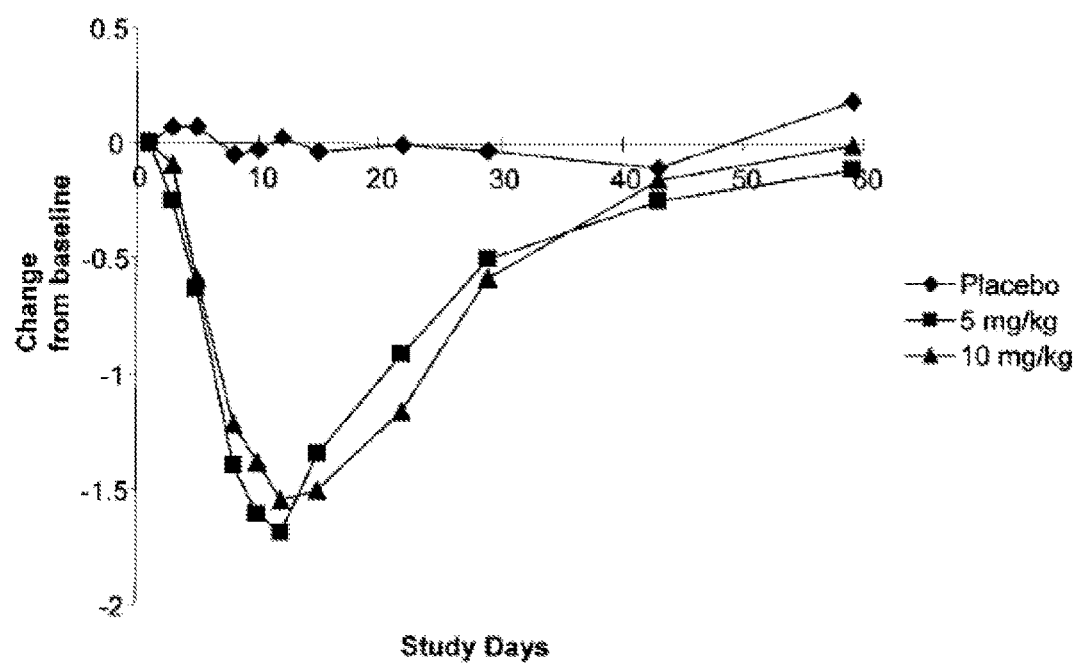

All PRO 140-treated subjects had more than 10-fold reduction in viral loads (mean max log$_{10}$ reductions were 1.83 for treatment groups and 0.32 for placebo) (FIG. 7). Both the 5 mg/kg and 10 mg/kg doses have shown favorable tolerability and no dose-limiting toxicity has been observed.

High levels of receptor occupancy (>85% reduction in the number of cells detected) were observed for 29 days after treatment with both 5 and 10 mg/kg doses.

In yet another prior study involving subcutaneous administration, PRO 140 was tested in HIV-infected subjects. The trial was a randomized, double-blind, placebo-controlled study in subjects (n=44) with early-stage, asymptomatic HIV infection, only R5 HIV-1 detectable, and no antiretroviral therapy for 12 weeks. Placebo (n=10) and three PRO 140 doses were examined: 162 mg weekly for three weeks (n=11), 324 mg weekly for three weeks (n=11), and 324 mg biweekly (every other week) for two doses (n=12). Subjects were followed for 44 days after the final dose. The study enrolled 40 males and 4 females. The median age, weight, CD4+ cell count and HIV-1 RNA at baseline were 42.3 years, 79.1 kg, 410 cells/μL and 20,000 copies/mL, respectively.

Figure 8A:
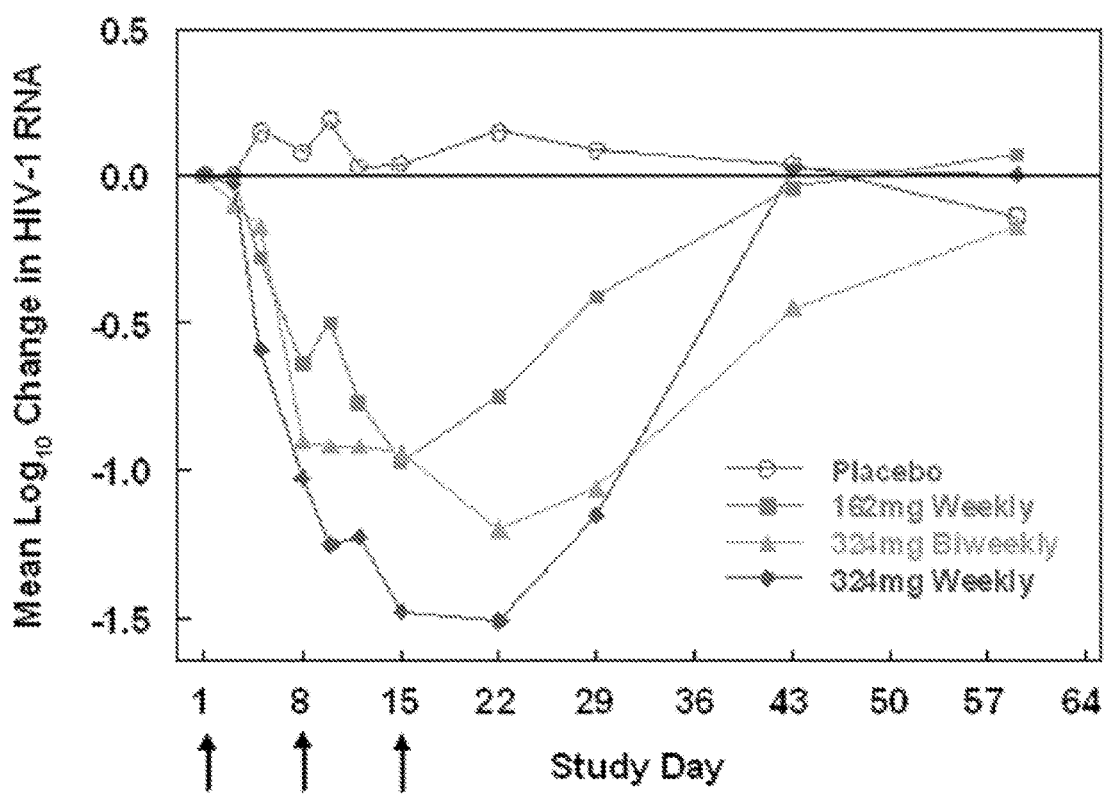
Figure 8B:
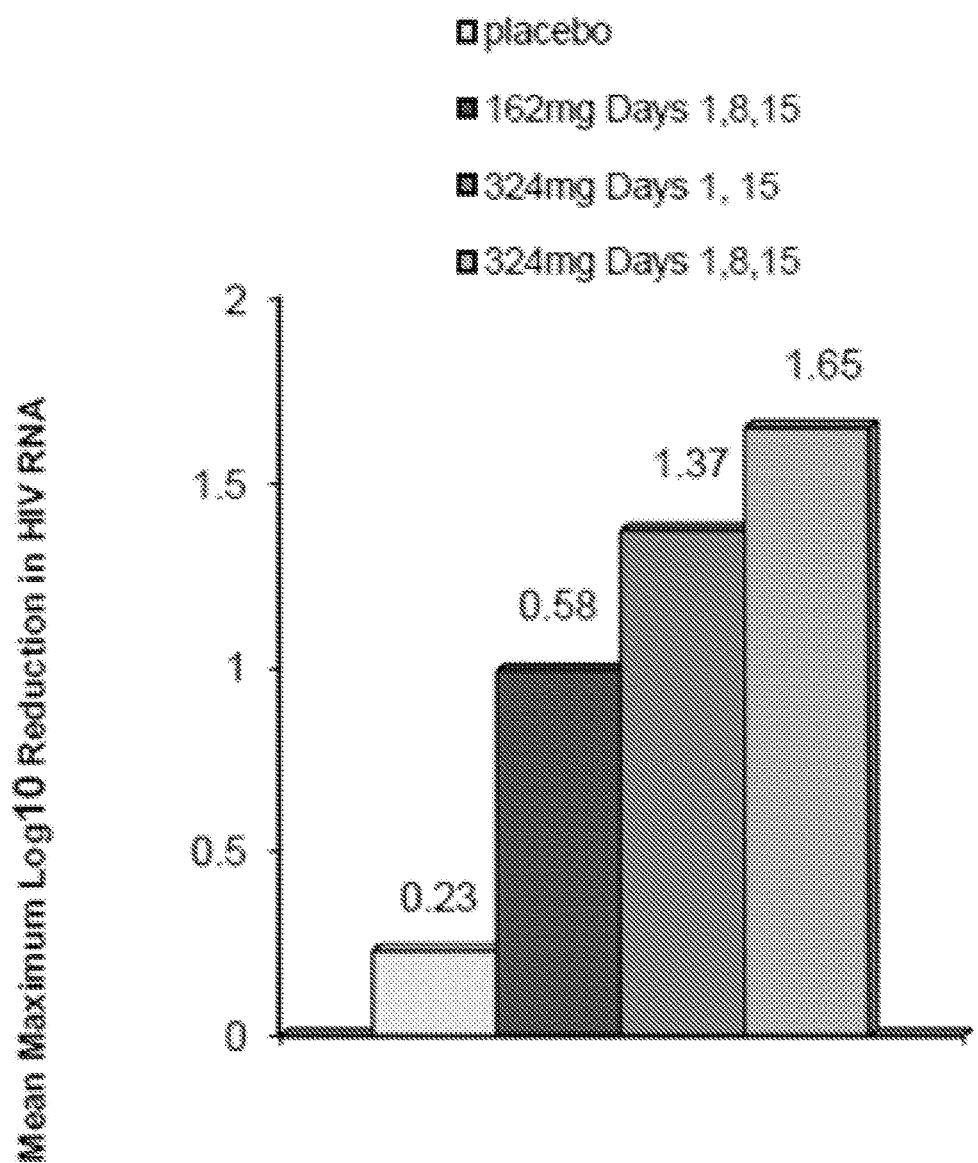
Figure 9:
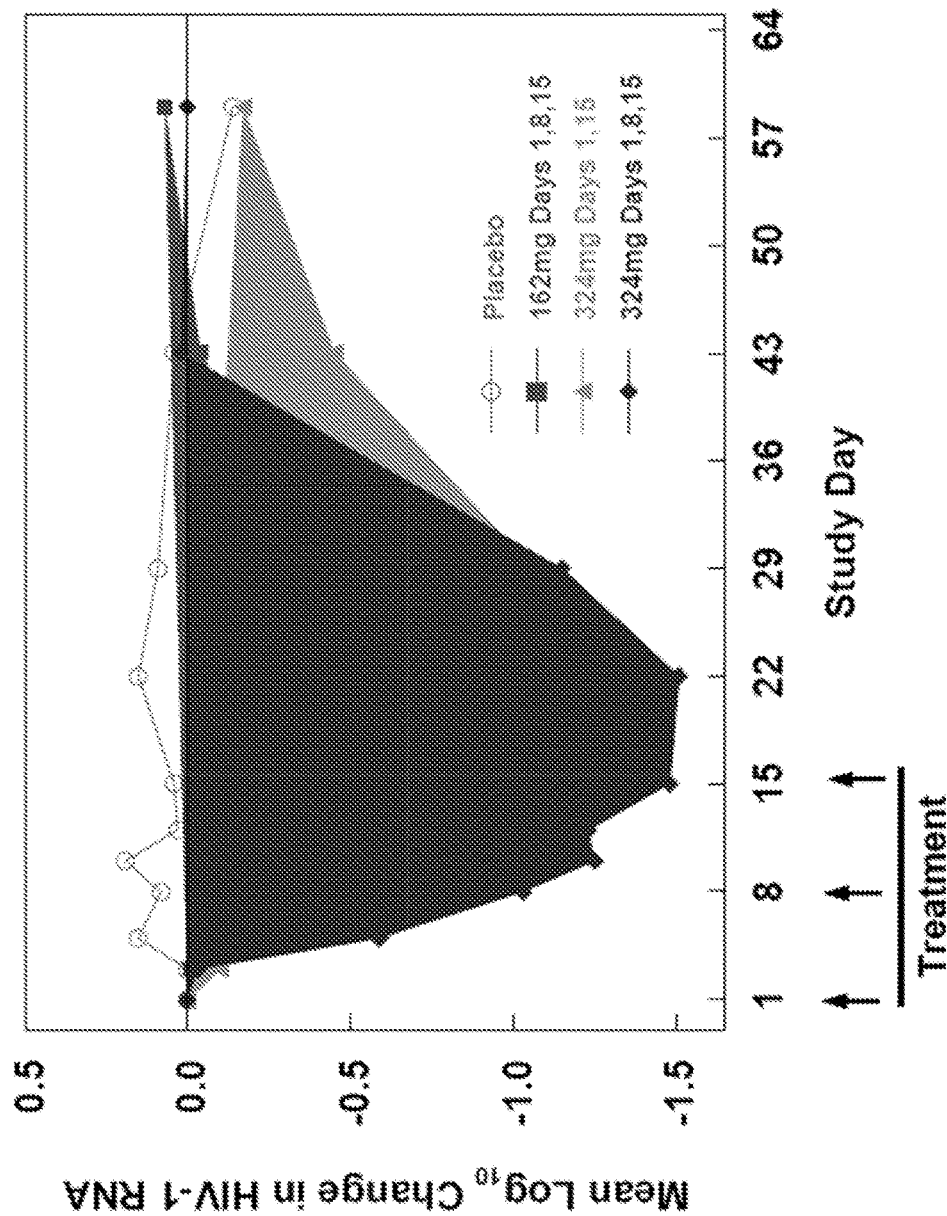
Figure 10A:
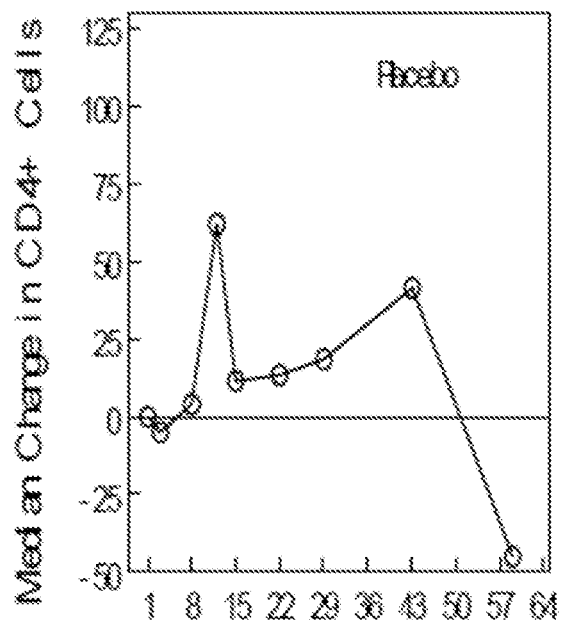
Figure 10B:
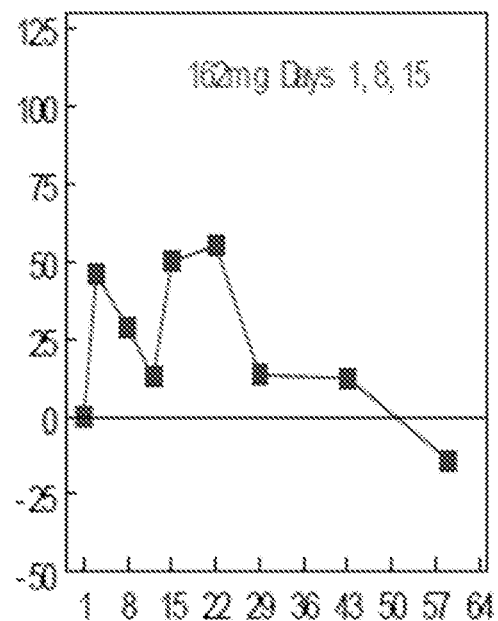
Figure 10C:
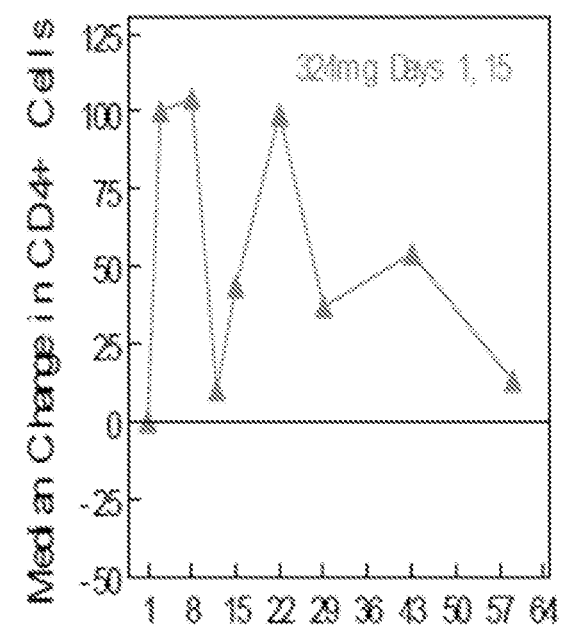
Figure 10D:
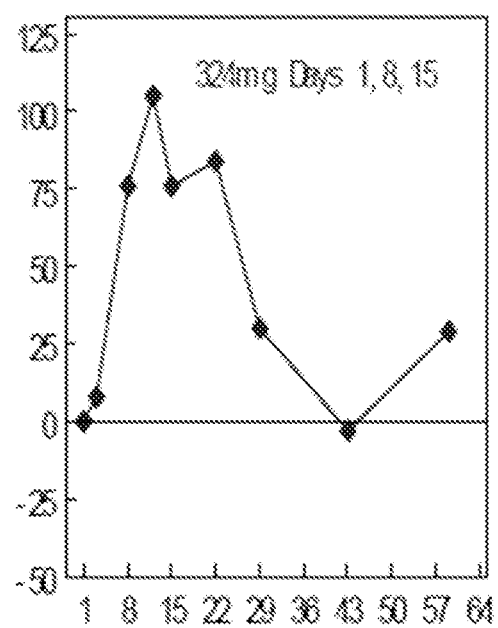

Baseline characteristics were similar for the different treatment groups. Potent, dose-dependent and highly statistically significant antiviral activity was observed (FIG. 8A, FIG. 8B, and FIG. 9). The 324 mg weekly dose resulted in a mean 1.65 $\log_{10}$ reduction in viral load, and highly significant reductions were observed for the other dose groups as well (FIG. 8A). There was no viral rebound between 324 mg doses, and the antiviral effects persisted for one week after the final dose (FIG. 9). The trial established the first antiviral proof of concept for a long-acting, self-administrable drug for HIV-1 infection.

Subcutaneous PRO 140 was generally well tolerated both locally and systemically. There was no obvious dose-related pattern of toxicity. The most common adverse events (diarrhea, headache, lymphadenopathy and hypertension) were mild to moderate and self-resolving. These events are common in HIV infection and were reported with similar frequencies in the placebo and PRO 140 treatment groups. Administration-site reactions were mild, transient, and observed in a fraction of subjects. There was a trend towards increased CD4+ cell counts in subjects treated with PRO 140 (FIGS. 10A, 10B, 10C, and 10D). Based on its encouraging antiviral and tolerability profiles and the convenience of weekly self-administration, SC PRO 140 has been selected for further clinical development.

As shown in FIGS. 10A, 10B, 10C, and 10D, Subjects (n=10 to 12 per group) were randomized to received placebo weekly (Days 1, 8, 15), 162 mg PRO 140 weekly (Days 1, 8, 15), 324 mg PRO 140 biweekly (Days 1, 15, with placebo on Day 8), or 324 mg PRO 140 weekly (Days 1, 8, 15). CD4+ cell counts were measured over time, and the median change from baseline was determined for each treatment group.

Phase 2b TS Study, Including Up to 12 Weeks of Exclusive PRO 140 Monotherapy

A first Phase 2b treatment substitution study was designed to investigate the potential for weekly injections of PRO 140, a fully humanized monoclonal antibody, to substitute for a patient's current drug regimen to allow a drug holiday. The study enrolled 40 patients in two cohorts, the first with 12 patients followed by a second cohort of 28 patients based on initial safety and efficacy data. All potential study patients were screened and for entry and must be HIV positive with the type of virus, 'R5', that uses the coreceptor CCR5 for cell entry and infection. Patients that have a strain of HIV, 'X4', that uses the other coreceptor, CXCR4, were excluded as PRO 140 is not effective in those patients. Each patient in the Phase 2b study continued the normal drug regimen plus PRO 140 for the first week, which was then followed by up to 12 weeks of PRO 140 monotherapy.

After 8 weeks of treatment substitution with PRO 140 monotherapy, half of the patients (six) experienced success. This Phase 2b study required oversight by an independent Data Safety Monitoring Board ("DSMB") to ensure patient safety and to assess efficacy. The DSMB met to review the interim clinical trial results data from the first cohort of 12 patients and noted no adverse reactions or side effects after three weeks of treatment. The DSMB then unanimously recommended that the study proceed with enrollment of the next 28-patient cohort to complete the 40-patient study.

As seen in FIG. 11, after four weeks of PRO 140 monotherapy, no patient experienced virologic failure and 100% of the patients passed four weeks of monotherapy.

Half the patients maintained suppressed viral loads after 8 weeks of monotherapy. Six patients, however, experienced virologic failures. The first of these 'failures' was documented to be a patient qualification screen failure rather than a drug failure. Applicant believes that this is a likely cause in the other failures. Virologic failures occurred as follows: three patients failed after five weeks of monotherapy, another one failed after six weeks of monotherapy and one additional patient failure occurred after eight weeks of monotherapy.

The TS Study interim results, after 8 weeks of monotherapy, showed no virologic failures in six patients. Of the six patients that had virologic failure, these were retested and two were confirmed to have dual-mix virus. Thus, excluding those two dual-mix virus patients, six of ten patients (60%) had viral load suppression after 8 weeks of monotherapy compared to nearly 0% in historical controls. After 10 weeks of monotherapy, five patients had not experienced virologic failure. After 11 weeks of monotherapy, 7 patients experienced virologic failure, and at least two of these patients were ruled out based on retesting that confirmed the presence of dual-mix virus.

The DSMB held a first meeting after two weeks of monotherapy and cleared enrollment of the second cohort of 28 subjects for entry into the study due to a lack of concerns related to safety and efficacy. The DSMB held a second meeting after six weeks of monotherapy and agreed that no safety issues were observed at that time.

One inclusion criterion for the Phase 2b study required each patient to have an undetectable viral load for the 12 months prior to enrollment. As only HIV patients who have R5 virus exclusively can benefit from PRO 140, each patient is required to take a DNA TROFILE® test prior to enrollment in the study. However, this test is only about 50% accurate in patients with an undetectable viral load. Therefore, the applicant expected to observe a number of viral rebounds due to inaccurate TROFILE® screening as observed thus far. Of the five patients who demonstrated a rebound in their viral load, at least one patient was retested and the test results concluded the patient had a "Dual/Mixed Tropic" HIV-1 virus and should have been excluded from the study. The applicant is investigating the possibility of developing a more accurate screening test for R5 exclusive virus among patients with undetectable virus.

TS with PRO 140 subcutaneous injection may be involve administration once per week, once every two weeks, and/or once per month. Possible TS scenarios include, for example, five months treatment with HAART, followed by one month treatment with PRO 140, or four months treatment with HAART, followed by two months treatment with PRO 140, or three months treatment with HAART, followed by three months treatment with PRO 140. It is also contemplated that PRO 140 may become the new baseline care, or a permanent or semi-permanent solution, for certain patients. That is treatment substation with PRO 140 may provide a permanent or semi-permanent, as opposed to intermittent or temporary, therapy option for certain patients.

First and Second Phase 2b TS Studies

The first phase 2b TS study, also noted above, was conducted based on the following protocol. The TS study was for the Human Immunodeficiency Virus Type-1 (HIV-1) Infection indication. The TS study involved forty patients, was 14 weeks long, and patients' viral loads were checked weekly. Patients enrolled in the study had undetectable viral load at day one of the study (viral load<50). Patients enrolled in the study took both PRO 140 and HAART regime drugs for the first week, and then only took PRO 140. Failure of a patient under study was determined to occur if their viral load (VL) was measured at >400 two times.

The primary objective was to assess efficacy of PRO 140 monotherapy for the maintenance of viral suppression following substitution of antiretroviral therapy in patients who are stable on combination antiretroviral therapy. The secondary objective of the trial was to assess the clinical safety and tolerability parameters following substitution of antiretroviral therapy in patients who are stable on combination antiretroviral therapy.

The primary efficacy endpoints were time to virologic failure after initiating PRO 140 monotherapy, wherein virologic failure was defined as two consecutive HIV-1 RNA levels of ≥400 copies/ml separated by at least 3 days. The secondary efficacy endpoints included the following: (1) proportion of participants with virologic failure after initiating PRO 140 monotherapy at or prior to Week 14; (2) mean change in Viral Load (HIV-1 RNA levels), at each visit within the 14-week treatment phase; (3) mean change in Viral Load (HIV-1 RNA levels), within the 14-week treatment phase; (4) mean change in CD4 cell count, at each visit within the 14-week treatment phase; (5) mean change in CD4 cell count, within the 14-week treatment phase; and (6) optionally, change in quality of life metrics Safety assessments included the following: (1) tolerability of repeated subcutaneous administration of PRO 140 as assessed by study participants (using Visual Analogue Scale) and by investigator-evaluation of injection site reactions; (2) frequency of Grade 3 or 4 adverse events as defined by the DAIDS adverse event scale; and (3) frequency of treatment-emergent serious adverse events.

The trial design was a Phase 2b, multi-center study designed to evaluate the efficacy, safety, and tolerability of PRO 140 monotherapy for the maintenance of viral suppression in patients who are stable on combination antiretroviral therapy.

Patient enrollment was staggered in this study to facilitate adequate safety monitoring. A lead cohort included 12 subjects. Enrollment of additional 28 subjects was initiated after approval by the independent DSMB. Consenting patients were shifted from combination antiretroviral regimen to PRO 140 monotherapy for 12 weeks. Total treatment duration with PRO 140 was up to 14 weeks with the one week overlap of existing retroviral regimen and PRO 140 at the beginning of the study treatment and also one week overlap at the end of the treatment in subjects who do not experience virologic failure.

PRO 140 was administered as a 350 mg subcutaneous injection weekly for up to 14 weeks. The PRO 140 350 mg subcutaneous injection was administered in two doses. Study participants were monitored for viral rebound on a weekly basis following initiation of PRO 140 monotherapy and re-initiated their previous antiretroviral regimen if plasma HIV-1 RNA levels rise above 400 copies/ml on two consecutive blood draws at least 3 days apart.

The study had three phases: Screening Phase, Treatment Phase and Follow-up Phase.

The Screening Phase (up to 42 days) was designed to determine whether subjects were eligible to proceed to the Treatment Phase of the study. This phase consisted of a series of screening assessments designed to determine eligibility. A written informed consent from the subject was obtained by the Investigator or suitably qualified individual before the performance of any protocol-specific procedure.

The Treatment Phase (up to 14 weeks) began with an evaluation of results of laboratory samples collected at the screening visit. Subjects who met all eligibility criteria, as per data gathered from Screening Visit were eligible for treatment. All subjects who failed to meet eligibility criteria were considered screen failures and exited the study without further evaluation. The first treatment visit took place within 42 days of the screening visit. Eligible subjects received up to 14 treatments, given every week (±3 days) or until virologic failure, whichever occurred first. Visits during the treatment phase commenced on T1, i.e. the date of first treatment, with weekly visits (±3 days) thereafter.

Efficacy assessments at each week included assessment of viral load and CD4 cells count. Safety assessments consisted of physical exam, lab, and adverse event assessments at each treatment and follow-up visit.

The study treatments (PRO 140 subcutaneous (SC) injections) were administered by a licensed medical professional (MD, DO, PA, LPN, LVN, NP, or RN).

All study subjects were set to re-initiate their previous antiretroviral regimen one week prior to the end of 14-week treatment phase, or during the treatment phase, if virologic failure occurred or if the subject met any other criteria for discontinuation of study treatment.

Subjects who experienced virologic failure (defined as two consecutive HIV-1 RNA levels of ≥400 copies/ml separated by at least 3 days) at any time during the treatment phase underwent the virologic failure (VF) visit assessments and then exited the Treatment Phase to enter the follow-up phase of the study. Subjects who do not experience VF were set to enter the follow-up phase of the study at the end of 14-week treatment phase.

Duration of follow-up phase was determined based on whether or not subject has experienced VF during the treatment phase. Subjects who experienced VF were followed up every 4 weeks until the viral suppression was achieved (i.e., plasma HIV-1 RNA levels to return back to <50 copies/mL). Subjects who did not experience VF at the end of 14-week treatment period, were followed up every 2 weeks for total of 4 weeks.

The initially scheduled duration of treatment included the following: a screening phase of up to 42 days and a treatment phase of 14 weeks±allowed windows (up to 14 treatments every week (±3 days)). After the treatment phase, a follow-up phase for those subjects with VF continued until viral suppression was achieved and, for those subject without VF, for four weeks. Thus, the total study duration was 24 weeks, not including the additional follow-up time for subjects with VF.

To be included in the Phase 2b study, potential subjects were required to meet all of the following criteria for enrollment into the study: (1) males and females, age≥18 years; (2) on stable antiretroviral therapy for last 12 months; (3) no change in antiretroviral regimen within last 4 weeks prior to screening visit and in-between screening visit and first treatment visit; (4) subject has two or more potential alternative antiretroviral regimen options to consider; (5) exclusive CCR5-tropic virus at screening visit as determined by TROFILE® DNA Assay; (6) plasma HIV-1 RNA<100 copies/mL at Screening Visit as determined by Human Immunodeficiency Virus 1 (HIV-1) Quantitative, RNA (Abbott RealTime); (7) no documented detectable viral loads (HIV-1 RNA<50 copies/ml) within the last 12 months prior to screening visit; (8) nadir CD4 cell count of ≥200 cells/mm$^3$; (9) CD4 cell count of >350 cells/mm$^3$ in preceding 6 months and at screening visit; (10) laboratory values at screening of a. absolute neutrophil count (ANC)≥1000/mm3, b. hemoglobin (Hb)≥11.5 gm/dL (male) or ≥10.5 gm/dL (female), c. platelets≥125,000/mm3, d. white blood cells (WBC)≥3000/mm3, e. serum alanine transaminase (SGPT/ALT)<5× upper limit of normal (ULN), f. serum aspartate transaminase (SGOT/AST)<5×ULN, g. bilirubin (total)<2.5×ULN unless in a subject receiving atazanavir and in the absence of other evidence of significant liver disease, and h. creatinine≤1.5×ULN; (11) clinically normal resting 12-lead ECG at screening visit or, if abnormal, considered not clinically significant by the Principal Investigator; (12) both male and female patients and their partners of childbearing potential must agree to use appropriate birth control methods (birth control pills, barriers, or abstinence) throughout the study duration (excluding women who are not of childbearing potential and men who have been sterilized). Females of childbearing potential must have a negative serum pregnancy test at Screening visit and negative urine pregnancy test prior to receiving the first dose of study drug; and (13) willing and able to participate in all aspects of the study, including use of SC medication, completion of subjective evaluations, attendance at scheduled clinic visits, and compliance with all protocol requirements as evidenced by providing written informed consent.

Exclusion criteria applied to any potential subjects meeting any of the following criteria will be excluded from enrollment: (1) CXCR4-tropic virus or dual/mixed tropic (R5X4) virus determined by the TROFILE® DNA Assay at the Screening Visit; (2) Hepatitis B infection as manifest by the presence of Hepatitis B surface antigen (HBsAg); (3) any acquired immune deficiency syndrome (AIDS)-defining illness according to the 1993 Centers for Disease Control and Prevention (CDC) AIDS surveillance definition; (4) laboratory test values≥grade 4 DAIDS laboratory abnormality; (5) females who were pregnant, lactating, or breastfeeding, or who plan to become pregnant during the study; (6) unexplained temperature>38.5° C. (101.3° F.) for seven consecutive days within 14 days prior to the first study dose; (7) subjects weighing<35 kg; (8) history of anaphylaxis; (9) history of Bleeding Disorder or patients on anti-coagulant therapy; (10) prior use of any entry, attachment, CCR5 co-receptor, or fusion inhibitor, including PRO 140; (11) participation in an experimental drug trial(s) within 30 days of the Screening Visit or during the study; (12) any known allergy or antibodies to the study drug or excipients; (13) treatment with any of the following: a. radiation or cytotoxic chemotherapy with 30 days prior to the screening visit or during the study, b. immunosuppressants within 60 days prior to the screening visit or during the study, c. immunomodulating agents (e.g., interleukins, interferons) or agents with known anti-HIV activity (i.e., hydroxyurea, foscarnet) within 60 days prior to the screening visit or during the study, d. oral or parenteral corticosteroids within 30 days prior to the screening visit or during the study; however, subjects on chronic steroid therapy>5 mg/day will be excluded with the following exceptions (i) subjects on chronic systemic corticosteroids at replacement doses (e.g., ≤5 mg/day prednisone) will not be excluded and (ii) subjects on inhaled, nasal, or topical steroids will not be excluded; (14) diagnosed with either substance dependence or substance abuse or any history of a concomitant condition (e.g., medical, psychological, or psychiatric) that in the opinion of the primary care provider and/or site investigator would interfere with the subject's successful completion of the study requirements; and (15) any other clinical condition that, in the Investigator's judgment, would potentially compromise study compliance or the ability to evaluate safety/efficacy.

The sample size of at least 40 subjects used in the trial was deemed adequate to provide clinically meaningful descriptive results consistent with study objectives.

The Intent-to-Treat (ITT) population was defined as the set of subjects who have at least one dose of PRO 140 and have at least one post-treatment efficacy assessment for viral load. The Per Protocol (PP) population was defined as the set of subjects who meet the ITT population requirements, and were not associated with a major protocol violation. This population was identified before the database lock. The PP population will be the primary analysis population for the analysis of primary and secondary endpoints. The Safety population was defined as all subjects who received at least one dose of PRO 140. This population will be used for the analysis of safety parameters.

There was no planned interim analysis (IA) for efficacy. Three IA for safety were conducted after the first 12 subjects completed the 4-weeks, 8-weeks and 14-weeks of treatment with PRO 140 or until treatment is discontinued, whichever came first. Three IA for safety were conducted for the second cohort of 28 subjects once the first 14 subjects complete 4-weeks, 8-weeks and 14-weeks of treatment with PRO 140 or until treatment was discontinued, whichever came first.

Efficacy Analysis. The main analysis of primary and secondary endpoint will be conducted on the PP population and ITT population will be used for supportive analysis. The primary efficacy endpoint for this study is time to VF after initiating PRO 140 monotherapy. VF is defined as two consecutive HIV-1 RNA levels of ≥400 copies/ml separated by at least 3 days. The time to VF for the subjects treated with PRO 140 monotherapy will be compared to a historical data (i.e., time to HIV-1 RNA viral load>500 copies/mL of 29 days). The statistical comparison will be conducted using Wilcoxon rank sum test and the median time to VF for this study will be compared to 30 days.

All the data from the secondary endpoint will also be summarized according to the variable type.

The secondary analysis includes consideration of the following: proportion of participants with VF after initiating PRO 140 monotherapy at or prior to Week 14; mean change in Viral Load (HIV-1 RNA levels), at each visit within the 14-week treatment phase; mean change in Viral Load, within the 14-week treatment phase; mean change in CD4 cell count, at each visit within the 14-week treatment phase; and mean change in CD4 cell count, within the 14-week treatment phase.

All data from the secondary endpoints are summarized according to the variable type for the PP population: Continuous data summaries include number of observations, mean, standard deviation, median, and minimum and maximum values; and categorical data summaries include frequency counts and percentages.

Dosages.

Figure 12:
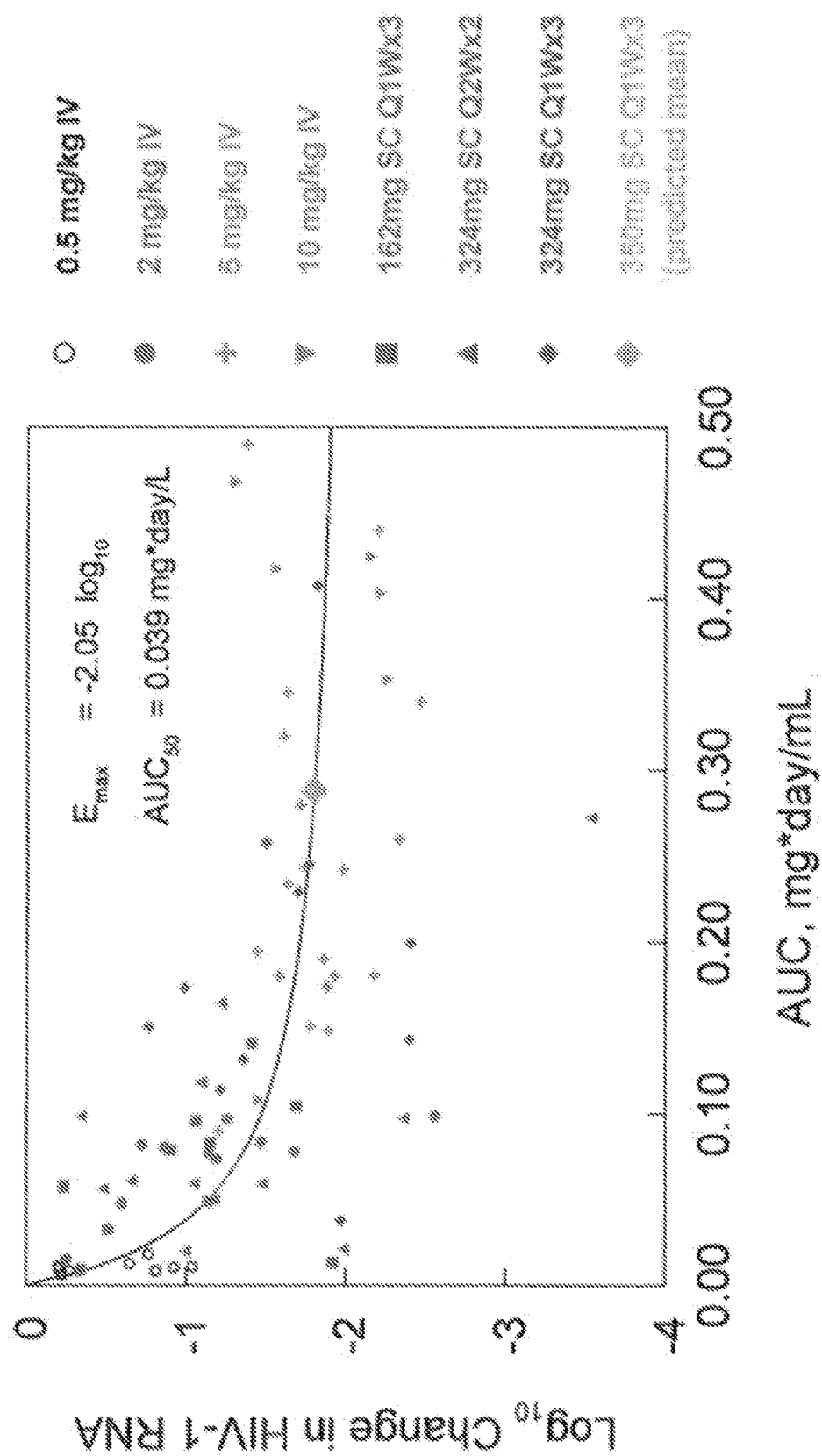
FIG. 12 shows the Emax analysis of antiviral data generated with IV and SC PRO 140, measure as Log$_{10}$ change in HIV-1 RNA versus AUC, mg*day/mL.

A dose of 350 mg administered SC was chosen in light of a previous analysis suggesting that such a dose would be likely to provide maximal viral load suppression. In studies with antiviral agents that block viral entry through the CCR5 receptor, there is a general consensus that in order to achieve robust antiviral effects and minimize the potential for drug resistance in combination therapy, the dose of drug should result in exposures that fall on the plateau of a Maximum Drug Effect (Emax) plot. The maximal viral load reduction was analyzed with regard to drug exposure for PRO 140. FIG. 12 shows this relationship. Analysis shows that PRO 140 350 mg weekly dose is expected to fall on the plateau of the Emax plot.

The maximal change in HIV-1 viral load from baseline was determined at any point 59 days after initiation of therapy. To allow approximate comparisons between the IV and SC doses, the overall AUC observed for repeat SC doses was conservatively estimated by multiplying the measured AUC0-7d by the number of doses administered. Viral load and AUC data were fit to an Emax equation: E=Emax×AUC/(AUC+AUC50). The diamond indicates projected data for three weekly 350 mg doses based on the mean exposure observed in a study.

It is important to note that when larger proteins (MW>10,000) are administered SC, they initially traffic through the lymphatic system. Uptake into the bloodstream occurs after the proteins reach the thoracic duct. As a consequence, a significant percentage of SC PRO 140 can be expected to encounter and bind CCR5-expressing cells and exert antiviral effects without ever reaching the bloodstream. For this reason, the serum AUC observed for SC administration may provide a conservative measure of drug exposure relative to that observed with IV administration.

In addition, based on pharmacodynamic data from our prior SC and IV studies, maximum virologic suppression is expected to be achieved with trough concentrations that equal or exceed approximately 5 µg/mL We expect that this target will be achieved by most or all of the dosing regimens to be studied.

Finally, the mean nadir reduction in viral load achieved with 3 weekly 324 mg SC doses (1.65 $\log_{10}$) was similar to the mean nadir reductions observed with single 5 or 10 mg/kg IV doses (1.8 $\log_{10}$ in each case), and higher viral load reductions are expected in the present study based on the use of the 350 mg formulation. Overall, several lines of evidence indicate that maximum virologic suppression will be achieved with 350 mg weekly dosing in the present study.

PRO 140 is a humanized IgG4,κ monoclonal antibody (mAb) to the chemokine receptor CCR5. PRO 140 is provided at a concentration of 175 mg/mL and is intended for SC route of administration. A total of 350 mg (175 mg/mL) is delivered as two 1 mL injections administered subcutaneously on opposite sides of the abdomen.

PRO 140 175 mg/mL was provided in 3 mL vials containing 1.4 mL of PRO 140 in a sterile buffered solution of 5 mM Histidine, 15 mM Glycine, 95 mM Sodium Chloride, 0.3% (w/v) Sorbitol, 0.005% (w/v) Polysorbate 20, at pH of 5.5. Note: 1 mL injection was to be drawn from 1.4 mL solution in a vial. Remaining 0.4 mL medication was to be discarded appropriately from each vial.

Study drug was shipped at 2° C. to 8° C. (refrigerated [36° F. to 46° F.]) to the investigator's site. Upon receipt at the site, the responsible site staff or pharmacist was to verify the integrity of the vials. Study drug should be stored at 2° C. to 8° C. (refrigerated [36° F. to 46° F.]). The contents of the vial should have appeared as a clear to opalescent, colorless to yellow solution; fine translucent particles may be present. This is normal.

PRO 140 was provided to the administering personnel in single-use syringes prepared from vials of study drug stored at 2-8° C. at the site pharmacy prior to use. Each of two syringes is filled to deliver 1.0 mL of study drug. Equivalent volumes of study drug will be administered subcutaneously on opposite sides of the abdomen. Following each SC delivery of drug, careful examination will be made to assess the appearance of any study drug Injection Site Reactions (ISRs) as described in Section 17.3.

All doses of study drug will be prepared by the credentialed pharmacist and will be administered as SC injection by a licensed medical professional.

Benefit.

This proof of concept study was for the purpose of selecting a dose and regimen for further clinical testing. The most significant limitation with highly active antiretroviral therapy (HAART) has been the necessity and challenge of continued daily adherence to the medications. This study provides opportunity to the subjects to have supervised once weekly SC treatment with PRO 140. Subjects participating in the present short term monotherapy study will contribute to the development of a drug which has the potential to become a treatment option for them and others in the future.

Study Objectives.

The primary objective was to assess efficacy of PRO 140 monotherapy for the maintenance of viral suppression following substitution of antiretroviral therapy in patients who are stable on combination antiretroviral therapy. The secondary objective of the trial was to assess the clinical safety and tolerability parameters following substitution of antiretroviral therapy in patients who are stable on combination antiretroviral therapy.

The primary efficacy endpoint for this study is time to Virologic Failure after initiating PRO 140 monotherapy. Virologic failure is defined as two consecutive HIV-1 RNA levels of ≥400 copies/ml separated by at least 3 days. The secondary efficacy endpoints will be proportion of participants with Virologic Failure after initiating PRO 140 monotherapy at or prior to Week 14, mean change in viral load (HIV-1 RNA levels), at each visit within the 14-week treatment phase, mean change in viral load (HIV-1 RNA levels), within the 14-week treatment phase, mean change in CD4 cell count, at each visit within the 14-week treatment phase and mean change in CD4 cell count, within the 14-week treatment phase and change in quality of life metrics.

Safety assessments include evaluation of tolerability of repeated subcutaneous administration of PRO 140 as assessed by study participants (using Visual Analogue Scale) and by investigator-evaluation of injection site reactions, frequency of Grade 3 or 4 adverse events and frequency of Treatment-emergent serious adverse events.

Study Flow and Schedule.

Figure 13:
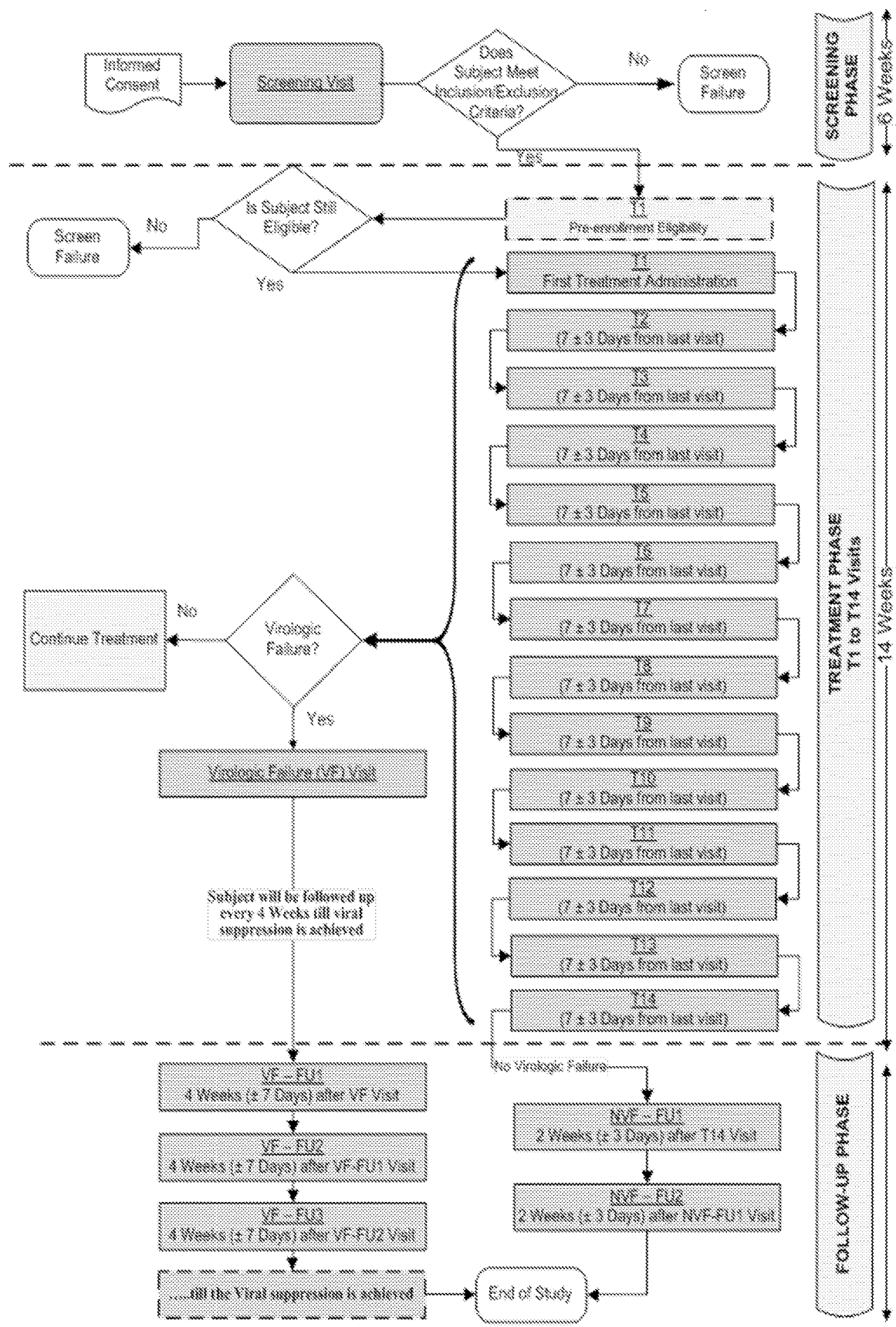
FIG. 13 shows the general study flow diagram for the first Phase 2b treatment substitution study.

FIG. 13 provides a flow chart of the study design. As previously noted, the study is divided into three study phases: (1) Screening Phase (Screening to T1 Visit) begins with signing of Informed Consent and lasts up to 6 weeks (42 days). First treatment will be administered within 42 days of the Screening Visit; (2) Treatment Phase (up to 14 weeks±allowed windows). Subjects will receive up to 14 treatments, given approximately every week (window period of ±3 days) or until viral suppression is maintained, whichever comes first. Any time during the Treatment Phase, if Virologic Failure occurs, subject will stop the study treatment and re-start their previous antiretroviral regimen. Treatment Phase begins with an evaluation of results of laboratory samples collected at the Screening Visit. Subjects who meet all eligibility criteria, as per data gathered from Screening Visit are to be treated. All subjects who fail to meet eligibility criteria will be considered screen failures and exit the study without further evaluation. Subjects will continue their existing antiretroviral regimen for one week after receiving initial dosing of PRO 140. Subjects will receive up to 14 treatments, given every week (±3 days) or until Virologic Failure, whichever occurs first.

Per the protocol, PRO 140 will be administered as a 350 mg subcutaneous injection weekly for up to 14 weeks. The study treatment (PRO 140 SC injections) will be administered by a licensed medical professional (MD, DO, PA, LPN, LVN, NP, or RN).

All study subjects will re-initiate their previous antiretroviral regimen: one week prior to the end of 14 week Treatment Phase, or anytime during the Treatment Phase, if Virologic Failure occurs or have met any other criteria for discontinuation of study treatment. Notably, in the case of an increase in plasma HIV-1 RNA levels above 200 copies/mL, subjects will return to clinic for another blood draw in-between the Treatment Visits for repeat plasma HIV-1 RNA levels, as per the discretion of the Investigator.

Subjects who experience Virologic Failure (defined as two consecutive HIV-1 RNA levels of ≥400 copies/ml separated by at least 3 days) at any time during the Treatment Phase will undergo the Virologic Failure (VF) Visit assessments and enter the Follow-up Phase of the study. Subjects who meet any criteria (other than Virologic Failure) for discontinuation of study treatment, will undergo T14 Visit assessments and enter the Follow-up Phase of the study. Subjects who do not experience Virologic Failure will enter the Follow-up Phase of the study at the end of 14-week Treatment Phase.

(3) Follow-Up Phase: The duration of follow-up depends on the status of viral load suppression. Subjects who experience Virologic Failure will be followed up every 4 weeks until the viral load suppression is achieved (i.e., plasma HIV-1 RNA levels to return back to <50 copies/mL). Subjects who do not experience Virologic Failure at the end of 14 week Treatment Period, will be followed up every 2 week for total of 4 weeks.

Results

A total of 40 subjects participated in the first Phase 2b PRO 140 Substitution study, of which 22 subjects completed the Treatment Phase without experiencing virologic failure. The trial was conducted in two cohorts. Only those subjects who have exclusive CCR5-tropic virus were to have been enrolled in this study. All 40 enrolled subjects were tested for HIV-1 co-receptor tropism and reported as having exclusive CCR5 tropism by the TROFILE® DNA Assay at the Screening Visit. However, 16 of the 40 subjects (40%) were later found to have Dual/Mixed HIV-1 RNA co-receptor tropism.

Thirty-nine (39) of out 40 (97.5%) enrolled subjects in this first PRO 140 Substitution study completed at least 4 weeks of PRO 140 monotherapy without experiencing virologic failure and 22 out of 40 (55%) enrolled subjects completed 12 weeks of PRO 140 Monotherapy without experiencing virologic failure.

Of the 40 enrolled subjects, 16 subjects were found to have Dual/Mixed tropism (D/M) and 24 subjects were found to have exclusive CCR5-tropic virus.

Thirty-three percent (33.3%) of R5-exclusive subjects compared to sixty-two percent (62.5%) of D/M subjects experienced virologic failure within 12 weeks of PRO 140 Monotherapy (Table 2).

TABLE 2

Summary of Virologic Failure, CCR5-plus Dual/Mixed-tropic Population

| Parameter | Total (N = 40) n/N | CCR5 (N = 24) n/N (%) | D/M (N = 16) n/N (%) |
|---|---|---|---|
| Proportion of Subjects with Virologic Failure within 4 weeks of PRO 140 Monotherapy | 1/40 | 1/24 (4.2%) | 0/16 (0.0%) |
| Proportion of Subjects with Virologic Failure within 12 weeks of PRO 140 Monotherapy | 18/40 | 8/24 (33.3%) | 10/16 (62.5%) |

N = number of CCR5- plus Dual/Mixed-tropic subjects within the population
n = number of subjects (or observations) within the population Overall, 18 out of 40 subjects (45%) experienced virologic failure during the 14 weeks of the Treatment Phase. All 18 subjects (8 in cohort-1 and 10 in cohort-2) with virologic failure re-initiated their prior oral antiretroviral regimen after confirmation of virologic failure. All virologic failure subjects (with an exception of subject 01-024 who was lost to follow-up) have achieved viral suppression to 'Non-Detectable' or <50 HIV-1 RNA copies/mL after experiencing virologic failure.

TABLE 3

Population Analysis

| Parameter | N = 40 n (%) |
|---|---|
| CCR5- plus Dual/Mixed-tropic population | 40 (100%) |
| Proportion of Subjects with Virologic Failure within 4 weeks of PRO 140 Monotherapy | 1 (2.5%) |
| Proportion of Subjects with Virologic Failure within 12 weeks of PRO 140 Monotherapy | 18 (45.0%) |
| Exclusive CCR5-tropic population | 24 (75%) |
| Proportion of Subjects with Virologic Failure within 4 weeks of PRO 140 Monotherapy | 1 (4.1%) |
| Proportion of Subjects with Virologic Failure within 12 weeks of PRO 140 Monotherapy | 8 (33.3%) |

N = number of subjects enrolled
n = number of subjects (or observations) within the population and the numerator for percentages As shown in Table 2 and Table, only one subject experienced virologic failure within 4 weeks of PRO 140 Monotherapy. Eighteen (18) out of 40 subjects (45%) experienced virologic failure during the 14-week Treatment Phase. Ten (10) subjects with virologic failure were found to have Dual- or Mixed-tropic virus, and eight (8) subjects had exclusive CCR5-tropic virus.

As a retrospective exploratory analysis, blood samples were also tested for HIV-1 Co-receptor Tropism by Proviral DNA method and Ultradeep Sequencing method (Quest Diagnostics). Combined analysis of tropism tests show 16 Dual/Mixed subjects were enrolled in the study and received the PRO 140 treatment. Based on the study data, 10 out of 16 Dual/Mixed subjects have had a virologic failure.

TABLE 4

Virologic Failure within 4 Weeks of PRO 140 Monotherapy
(T6 Visit), Exclusive CCR5-tropic Population

| Parameter | N = 24<br>n (%) |
|---|---|
| Virologic Failure within 4 weeks | 1 (4.2%) |
| Without Virologic Failure within 4 weeks | 23 (95.8%) |

N = number of Exclusive CCR5-tropic subjects completed at least 4 weeks of PRO 140 monotherapy
n = number of subjects (or observations) within the population and the numerator for percentages

TABLE 5

Virologic Failure within 4 Weeks of PRO 140 Monotherapy
(T6 Visit), CCR5- plus Dual/Mixed-tropic Population

| Parameter | N = 40<br>n (%) |
|---|---|
| Virologic Failure within 4 weeks | 1 (2.5%) |
| Without Virologic Failure within 4 weeks | 39 (97.5%) |

N = number of CCR5- plus Dual/Mixed-tropic subjects completed at least 4 weeks of PRO 140 monotherapy
n = number of subjects (or observations) within the population and the numerator for percentages

TABLE 6

Virologic Failure anytime during the Treatment
Phase, Exclusive CCR5-tropic Population

| Parameter | N = 24<br>n (%) |
|---|---|
| Virologic Failure anytime during Treatment Phase | 8 (30.4%) |
| Without Virologic Failure anytime during Treatment Phase | 16 (69.5%) |

N = number of Exclusive CCR5-tropic subjects within the population
n = number of subjects (or observations) within the population and the numerator for percentages

TABLE 7

Virologic Failure anytime during the Treatment
Phase, CCR5- plus Dual/Mixed-tropic Population

| Parameter | N = 40<br>n (%) |
|---|---|
| Virologic Failure anytime during Treatment Phase | 18 (20.5%) |
| Without Virologic Failure anytime during Treatment Phase | 22 (79.5%) |

N = number of CCR5- plus Dual/Mixed-tropic subjects within the population
n = number of subjects (or observations) within the population and the numerator for percentages For these 40 subjects, CD4 cell counts (/mm$^3$) and HIV-1 RNA levels (copies/mL) were measured. The table 8 below shows the subject specific CD4 cell count and plasma HIV-1 RNA levels for up to 4 weeks of PRO 140 monotherapy (T6 Visit).

TABLE 8

| Subject ID | Visit | CD4 cell count (/mm^3) | HIV-1 RNA Level (copies/mL) |
|---|---|---|---|
| A | SV |  | TND |
|  | T1 | 508 | TND |
|  | T2 | 426 | TND |
|  | T3 | 513 | TND |
|  | T4 | 468 | TND |
|  | T5 | 585 | TND |
|  | T6 | 611 | TND |
| B | SV |  | TND |
|  | T1 | 519 | TND |
|  | T2 | 466 | TND |
|  | T3 | 585 | TND |
|  | T4 | 472 | <40 |
|  | T5 | 465 | 385 |
|  | T6 | 414 | 1891 |
| C | SV |  | TND |
|  | T1 | 805 | TND |
|  | T2 | 833 | TND |
|  | T3 | 962 | <40 |
|  | T4 | 740 | TND |
|  | T5 | 994 | <40 |
|  | T6 | 897 | TND |
| D | SV |  | TND |
|  | T1 | 476 | <40 |
|  | T2 | 568 | TND |
|  | T3 | 667 | TND |
|  | T4 | 442 | TND |
|  | T5 |  | <40 |
|  | T6 | 578 | 310 |
| E | SV |  | <40 |
|  | T1 | 864 | TND |
|  | T2 | 757 | <40 |
|  | T3 | 755 | TND |
|  | T4 | 653 | TND |
|  | T5 | 704 | TND |
|  | T6 | 686 | <40 |
| F | SV |  | TND |
|  | T1 | 1014 | TND |
|  | T2 | 691 | TND |
|  | T3 | 1299 | TND |
|  | T4 | 1095 | <40 |
|  | T5 | 831 | TND |
|  | T6 | 771 | <40 |
| G | SV |  | TND |
|  | T1 | 683 | TND |
|  | T2 | 571 | TND |
|  | T3 | 677 | <40 |
|  | T4 | 652 | <40 |
|  | T5 | 642 | <40 |
|  | T6 | 607 | 68 |
| H | SV |  | TND |
|  | T1 | 627 | <40 |
|  | T2 | 357 | TND |
|  | T3 | 497 | TND |
|  | T4 | 594 | <40 |
|  | T5 | 509 | <40 |
|  | T6 | 481 | 74 |
| I | SV |  | <40 |
|  | T1 | 524 | 57 |
|  | T2 | 451 | TND |
|  | T3 | 443 | <40 |
|  | T4 | 633 | 40 |
|  | T5 | 514 | TND |
|  | T6 | 480 | <40 |
| J | SV |  | TND |
|  | T1 | 833 | TND |
|  | T2 | 628 | TND |
|  | T3 | 625 | TND |
|  | T4 | 677 | TND |
|  | T5 | 859 | TND |
|  | T6 | 726 | 138 |
| K | SV |  | TND |
|  | T1 | 513 | TND |
|  | T2 | 570 | TND |
|  | T3 | 554 | TND |
|  | T4 | 659 | <40 |
|  | T5 | 665 | <40 |
|  | T6 | 575 | TND |
| L | SV |  | TND |
|  | T1 | 785 | TND |
|  | T2 | 711 | TND |

TABLE 8-continued

| Subject ID | Visit | CD4 cell count (/mm^3) | HIV-1 RNA Level (copies/mL) |
|---|---|---|---|
|  | T3 | 901 | TND |
|  | T4 | 703 | TND |
|  | T5 | 785 | 40 |
|  | T6 | 667 | 2769 |
| M | SV |  | TND |
|  | T1 | 868 | TND |
|  | T2 | 733 | <40 |
|  | T3 | 858 | TND |
|  | T4 | 754 | <40 |
|  | T5 | 646 | 148 |
|  | T6 | 732 | 2074 |
| N | SV |  | TND |
|  | T1 | 576 | TND |
|  | T2 | 604 | TND |
|  | T3 |  | TND |
|  | T4 | 726 | <40 |
|  | T5 |  | <40 |
|  | T6 | 716 | <40 |
| O | SV |  | TND |
|  | T1 | 291 | TND |
|  | T2 | 272 | TND |
|  | T3 |  | TND |
|  | T4 | 355 | <40 |
|  | T5 |  | <40 |
|  | T6 | 330 | <40 |
| 1 | SV |  | TND |
|  | SV | 815 | TND |
|  | T1 | 679 | TND |
|  | T2 | 674 | TND |
|  | T3 |  | TND |
|  | T4 | 800 | TND |
|  | T5 |  | TND |
|  | T6 | 795 | TND |
| 2 | SV | 582 | TND |
|  | SV | 477 | TND |
|  | T1 | 487 | TND |
|  | T2 | 449 | TND |
|  | T3 |  | TND |
|  | T4 | 573 | TND |
|  | T5 |  | TND |
|  | T6 | 632 | TND |
| P | SV | 694 | TND |
|  | SV | 813 | <40 |
|  | T1 | 724 | TND |
|  | T2 | 709 | TND |
|  | T3 |  | TND |
|  | T4 | 641 | <40 |
|  | T5 |  | TND |
|  | T6 | 818 | <40 |
| 3 | SV | 735 | TND |
|  | SV | 618 |  |
|  | T1 | 459 | TND |
|  | T2 | 546 | TND |
|  | T3 |  | TND |
|  | T4 | 598 | TND |
|  | T5 |  | TND |
|  | T6 | 476 | TND |
| 4 | SV | 629 | TND |
|  | SV | 600 | TND |
|  | T1 | 679 | TND |
|  | T2 | 669 | TND |
|  | T3 |  | TND |
|  | T4 | 849 | TND |
|  | T5 |  | TND |
|  | T6 | 743 | TND |
| 5 | SV | 379 | TND |
|  | T1 | 295 | TND |
|  | T2 | 400 | TND |
|  | T3 |  | TND |
|  | T4 | 392 | TND |
|  | T5 |  | TND |
|  | T6 | 341 | TND |
| 6 | SV | 396 | TND |
|  | SV | 545 | TND |
|  | T1 | 777 | TND |
|  | T2 | 530 | TND |
|  | T3 |  | TND |
|  | T4 | 632 | TND |
|  | T5 |  | TND |
|  | T6 | 648 | TND |
| Q | SV | 636 | TND |
|  | SV | 827 | TND |
|  | T1 | 561 | TND |
|  | T2 | 566 | TND |
|  | T3 |  | TND |
|  | T4 | 465 | TND |
|  | T5 |  | 104 |
|  | T6 | 553 | 2153 |
| R | SV | 923 | TND |
|  | SV | 1063 |  |
|  | T1 | 924 | 42 |
|  | T2 | 1231 | <40 |
|  | T3 |  | TND |
|  | T4 | 1023 | <40 |
|  | T5 |  | TND |
|  | T6 | 1135 | <40 |
| S | SV | 514 | TND |
|  | SV | 526 | TND |
|  | T1 | 448 | TND |
|  | T2 | 566 | TND |
|  | T3 |  | TND |
|  | T4 | 640 | TND |
|  | T5 |  | TND |
|  | T6 | 672 | 2153 |
| T | SV | 1102 | TND |
|  | T1 | 954 | TND |
|  | T2 | 939 | TND |
|  | T3 | 1043 | <40 |
|  | T4 | 1308 | TND |
|  | T5 |  | <40 |
|  | T6 | 965 | 163 |
| 7 | SV | 447 | <40 |
|  | T1 | 467 | <40 |
|  | T2 | 364 | <40 |
|  | T3 |  | TND |
|  | T4 | 296 | <40 |
|  | T5 | 356 | <40 |
|  | T6 | 331 | TND |
| U | SV | 768 | <40 |
|  | T1 | 433 | 43 |
|  | T2 | 577 | <40 |
|  | T3 |  | <40 |
|  | T4 | 641 | <40 |
|  | T5 |  | TND |
|  | T6 | 701 | <40 |
| V | SV | 702 | <40 |
|  | T1 | 636 | <40 |
|  | T2 | 733 | <40 |
|  | T3 | 760 | TND |
|  | T4 | 798 | TND |
|  | T5 |  | TND |
|  | T6 | 656 | TND |
| 8 | SV | 387 | TND |
|  | SV | 304 | TND |
|  | SV | 685 |  |
|  | T1 | 510 | 61 |
|  | T2 | 531 | TND |
|  | T3 |  | <40 |
|  | T4 | 532 | <40 |
|  | T5 |  | <40 |
|  | T6 | 485 | <40 |
| 9 | SV | 609 | TND |
|  | T1 | 665 | <40 |
|  | T2 | 633 | TND |
|  | T3 |  | TND |
|  | T4 | 684 | TND |
|  | T5 |  | TND |
|  | T6 | 574 | TND |
| W | SV | 1059 | TND |
|  | T1 | 1099 | TND |
|  | T2 | 1052 | <40 |
|  | T3 |  | TND |

TABLE 8-continued

| Subject ID | Visit | CD4 cell count (/mm^3) | HIV-1 RNA Level (copies/mL) |
|---|---|---|---|
|  | T4 | 1016 | <40 |
|  | T5 |  | <40 |
|  | T6 | 1063 | <40 |
| 10 | SV | 777 | TND |
|  | T1 | 697 | TND |
|  | T2 | 787 | TND |
|  | T3 |  | TND |
|  | T4 | 606 | <40 |
|  | T5 |  | TND |
|  | T6 | 746 | TND |
| 11 | SV | 586 | TND |
|  | T1 | 830 | TND |
|  | T2 | 518 | TND |
|  | T3 |  | TND |
|  | T4 | 601 | TND |
|  | T5 |  | TND |
|  | T6 | 666 | TND |
| 12 | SV | 344 | TND |
|  | SV | 396 |  |
|  | T1 | 492 | TND |
|  | T2 | 399 | TND |
|  | T3 |  | TND |
|  | T4 | 505 | TND |
|  | T5 |  | TND |
|  | T6 | 383 | TND |
| X | SV | 706 | <40 |
|  | T1 | 951 | TND |
|  | T2 | 939 | <40 |
|  | T3 |  | <40 |
|  | T4 | 665 | TND |
|  | T5 |  | 1282 |
|  | T6 | 742 | 10925 |
| 13 | SV | 365 | <40 |
|  | T1 | 443 | TND |
|  | T2 | 494 | TND |
|  | T3 |  | TND |
|  | T4 | 483 | TND |
|  | T5 |  | TND |
|  | T6 | 480 | TND |
| Y | SV | 803 | TND |
|  | T1 | 757 | TND |
|  | T2 | 750 | TND |
|  | T3 |  | <40 |
|  | T4 | 859 | TND |
|  | T5 |  | TND |
|  | T6 | 769 | 76 |
| 14 | SV | 477 | TND |
|  | T1 | 511 | <40 |
|  | T2 | 632 | TND |
|  | T3 |  | <40 |
|  | T4 | 538 | <40 |
|  | T5 |  | <40 |
|  | T6 | 689 | TND |
| Z | SV | 484 | TND |
|  | T1 | 671 | TND |
|  | T2 | 405 | TND |
|  | T3 |  | TND |
|  | T4 | 587 | TND |
|  | T5 |  | TND |
|  | T6 | N/A | TND |

Figure 14:
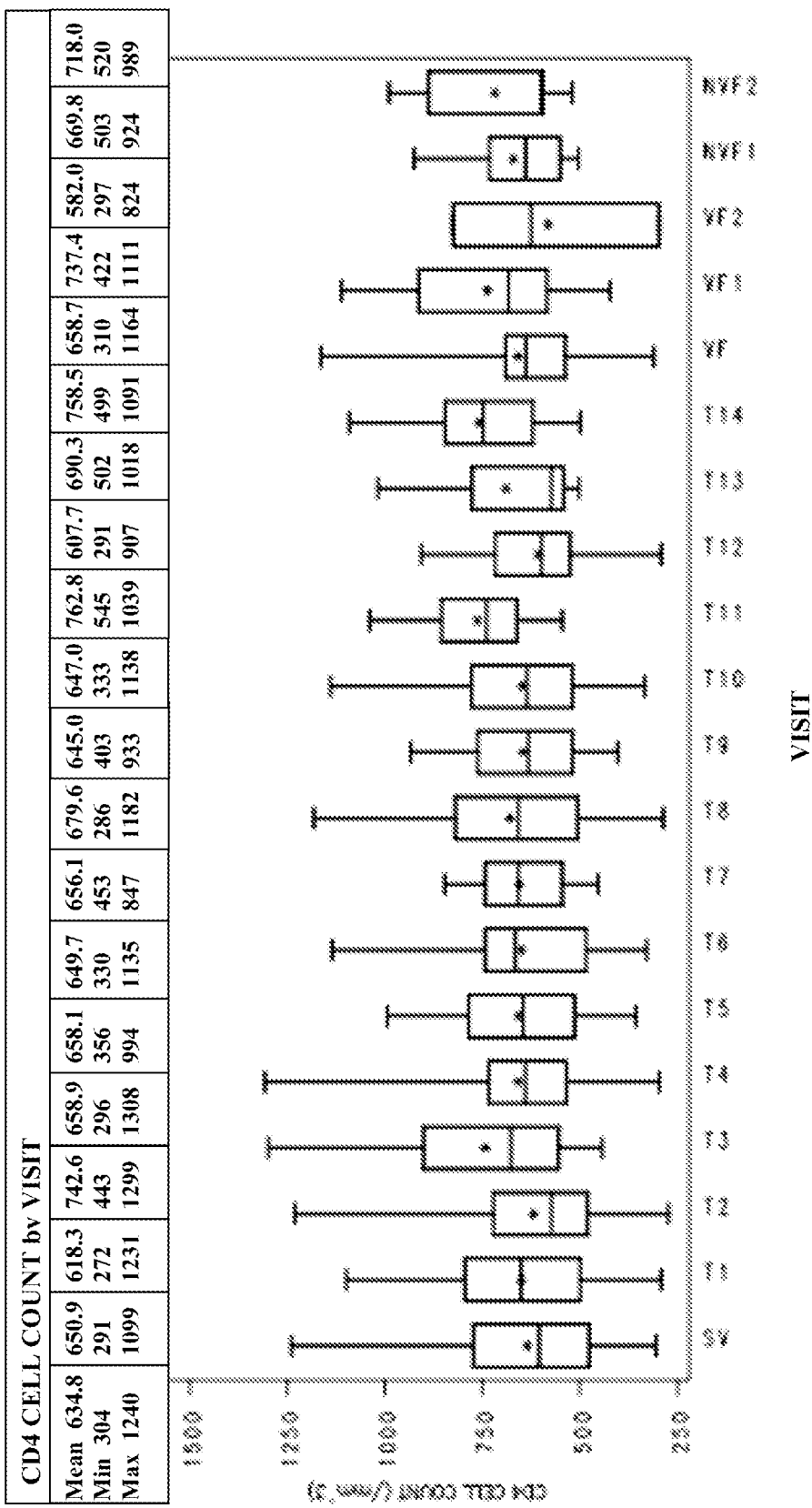
FIG. 14 shows the CD4 cell count for participants in the first Phase 2b treatment substitution study, measured as CD4 cell count (/mm$^{-3}$) versus various time points.

Overall review of results indicates that CD4 cell counts were maintained at stable levels throughout the Treatment Phase. See FIG. 14.

Seventeen of out of eighteen (18) virologic failure subjects (94.4%) achieved viral suppression to <400 HIV-1 RNA copies/ml, as well as viral suppression to 'Non Detectable' or <50 HIV-1 RNA copies/ml once ART reinitiated after virologic failure confirmed. No significant change to the HIV-1 RNA virus or $IC_{50}$ values observed as a result of exposure to PRO 140 monotherapy during the 14-week Treatment Phase for the 18 subjects with virologic failure. Additionally, PK samples were analyzed and there is no significant difference observed in subjects that did not experience virologic failure.

All 18 subjects (8 subjects in cohort-1 and 10 subjects in cohort-2) with virologic failure re-initiated their prior oral antiretroviral regimen after the confirmation of virologic failure. All 8 virologic failure subjects (100%) in the first cohort have achieved viral suppression to <400 HIV-1 RNA copies/ml, as well as viral suppression to 'Non Detectable' or <50 HIV-1 RNA copies/ml. Nine (9) of 10 subjects in the second cohort have achieved viral suppression to <400 HIV-1 RNA copies/ml, as well as viral suppression to 'Non Detectable' or <50 HIV-1 RNA copies/ml. The remaining subject in the second cohort was documented as lost to Follow-Up.

The subject-specific listing of Time to HIV-1 RNA levels of <400 copies/ml and <50 copies/ml is presented in Table 9 below.

TABLE 9

Time to Viral Suppression, Virologic Failure Subjects

| Subject ID | Time to Breakthrough (Days) | Time to Virologic Failure (Days) | HIV-1 RNA Level <400 | | HIV-1 RNA Level <50 | |
|---|---|---|---|---|---|---|
|  |  |  | Viral Load (copies/mL) | Time (Days) from Virologic Failure | Viral Load (copies/mL) | Time (Days) from Virologic Failure |
| B | 29 | 36 | <40 | 36 | <40 | 36 |
| C | 64 | 71 | 353 | 43 | 0 | 94 |
| G | 71 | 78 | 53 | 7 | <40 | 22 |
| H | 43 | 50 | <40 | 43 | <40 | 43 |
| J | 35 | 40 | TND | 37 | TND | 37 |
| K | 43 | 50 | 62 | 64 | 43 | 71 |
| L | 29 | 36 | <40 | 29 | <40 | 29 |
| M | 29 | 36 | 278 | 29 | <40 | 95 |
| N | 37 | 43 | <40 | 8 | <40 | 8 |
| O | 64 | 71 | n/a | n/a | n/a | n/a |
| P | 64 | 71 | 166 | 4 | TND | 55 |
| Q | 29 | 36 | 126 | 36 | <40 | 71 |

TABLE 9-continued

Time to Viral Suppression, Virologic Failure Subjects

| Subject ID | Time to Breakthrough (Days) | Time to Virologic Failure (Days) | HIV-1 RNA Level <400 | | HIV-1 RNA Level <50 | |
|---|---|---|---|---|---|---|
| | | | Viral Load (copies/mL) | Time (Days) from Virologic Failure | Viral Load (copies/mL) | Time (Days) from Virologic Failure |
| R | 55 | 63 | <40 | 42 | <40 | 42 |
| S | 29 | 36 | <40 | 31 | <40 | 31 |
| T | 36 | 43 | <40 | 43 | <40 | 43 |
| X | 21 | 28 | 48 | 37 | 48 | 37 |
| Y | 57 | 64 | <40 | 43 | <40 | 43 |
| Z | 50 | 57 | 166 | 8 | TND | 43 |

Note:
CD4 cell count assessed every other visit beyond T2 for subjects enrolled in Cohort-2

TABLE 10

List of subjects reported as Dual/Mixed, CD 01 Substitution

| Subject ID | Virologic Failure | If no Virologic Failure, Last Treatment Visit Completed | Time to Virologic Failure (Days) | Plasma HIV-1 RNA Level (copies/mL) |
|---|---|---|---|---|
| B | YES | | 36 | 16304 |
| J | YES | | 40 | 3311 |
| M | YES | | 36 | 28502 |
| O | YES | | 71 | 2088 |
| P | YES | | 71 | 3092 |
| 3 | NO* | T14 | | |
| 4 | NO* | T14 | | |
| 5 | NO* | T14 | | |
| Q | YES | | 36 | 7261 |
| S | YES | | 36 | 148594 |
| T | YES | | 43 | 1811 |
| U | NO* | T14 | | |
| 9 | NO* | T14 | | |
| Y | YES | | 64 | 434 |
| 14 | NO* | T14 | | |
| Z | YES | | 57 | 2073 |

*Completed Treatment Phase and enrolled in CD01-Extension study

Data regarding adverse events include 28 of 40 subjects who experienced one or more adverse events after receiving at least one dose of PRO 140. The most commonly occurring AEs are 'infections and infestations' which were reported by 14 of 40 subjects (35%), followed by 'general disorders and administration site conditions' which were reported by 13 of 40 subjects (32.5%).

Safety data was analyzed for all 40 subjects in the CCR5-plus Dual/Mixed-tropic population. One (1) of 40 subjects experienced an SAE that was deemed not related to the study drug. Twenty-eight (28) of 40 subjects experienced one or more adverse events (AEs) after receiving at least one dose of PRO 140. The most commonly occurring AEs are infections and infestation conditions which were reported by 14 of 40 (35%) subjects. The majority of the reported AEs (63/89; 70.7%) were deemed either unlikely or not related to study treatment by the Investigator. Similarly, the majority of the reported AEs (72/89; 80.8%) were deemed mild in nature.

Second Phase 2b Extension TS Study, Including Up to 28 Subjects and 60 Additional Weeks of Exclusive PRO 140 Monotherapy An extension study using the protocol established for the first Phase 2b TS study was undertaken to further evaluate the long-term suppression of HIV-1 replication following substitution of stable combination antiretroviral therapy with a PRO 140 (Monoclonal CCR5 antibody) monotherapy for an additional 60 weeks in adult subjects with HIV-1 infection. The primary objective is to assess the long-term efficacy of PRO 140 monotherapy for the maintenance of viral suppression in patients who have completed 12 weeks of treatment in the first TS study without experiencing virologic failure. The secondary objectives of the trial are to assess the long-term clinical safety and tolerability parameters of continued PRO 140 use in patients who have completed 12 weeks of treatment in the first TS study without experiencing virologic failure.

At least 16 subjects from the first TS study participated in the PRO 140 Extension study. The total additional treatment duration with PRO 140 is up to 60 weeks with subjects having the same one-week overlap of existing retroviral regimen and PRO 140 from the beginning of the PRO 140 Substitution study and a one week overlap of existing retroviral regimen and PRO 140 at end of the Treatment Extension Phase. Only subjects in cohort-2 who completed the first 12 weeks of PRO 140 monotherapy in the PRO 140 Substitution study without experiencing virologic failure were eligible to continue PRO 140 monotherapy.

The primary efficacy endpoints are the time to virologic failure after initiating PRO 140 monotherapy, wherein virologic failure is defined as two consecutive HIV-1 RNA levels of ≥400 copies/ml separated by at least 3 days. The time to virologic failure for the subjects treated with PRO 140 monotherapy will be compared to a historical data (i.e., time to HIV-1 RNA viral load>500 copies/mL of 29 days). The statistical comparison will be conducted using Wilcoxon rank sum test and the median time to virologic failure for this study will be compared to 30 days.

The secondary efficacy endpoints include the proportion of Participants with virologic failure after initiating PRO 140 monotherapy, the mean change in viral load (HIV-1 RNA levels), the mean change in CD4 cell count, and the change in Quality of Life metrics. All the data from the secondary endpoint will also be summarized according to the variable type.

Safety based on the tolerability of repeated subcutaneous administration of PRO 140 as assessed by study participants (using Visual Analogue Scale) and by investigator-evaluation of injection site reactions, frequency of Grade 3 (severe or medically significant but not immediately life-threatening; hospitalization or prolongation of hospitalization indicated; disabling; limiting self-care) or Grade 4 (Life-threatening consequences; urgent intervention indicated) adverse events as defined by the DAIDS Adverse Event scale, and frequency of treatment-emergent serious adverse events. An adverse event (AE) is defined as any unfavorable or unintended sign, symptom, or disease that occurs or is reported by the subject to have occurred, or a worsening of a pre-existing condition. An AE may or may not be related to the study treatment.

This second Phase 2b Extension TS Study is a multicenter, extension study designed to evaluate the long-term efficacy, safety, and tolerability of PRO 140 monotherapy for the maintenance of viral suppression in patients who were stable on combination antiretroviral therapy and completed 12 weeks of treatment under the first TS study without experiencing virologic failure. Consenting patients continue to receive PRO 140 monotherapy for 60 additional weeks. Total treatment duration with PRO 140 is up to 61 weeks with one week overlap of existing retroviral regimen and PRO 140 at the end of the treatment extension phase in subjects who do not experience virologic failure. PRO 140 is administered as a 350 mg subcutaneous injection weekly for up to 61 weeks. Study participants are monitored for viral rebound on a weekly basis following initiation of PRO 140 monotherapy and will re-initiate their previous antiretroviral regimen if plasma HIV-1 RNA levels rise above 400 copies/ml on two consecutive blood draws at least 3 days apart.

Figure 15:
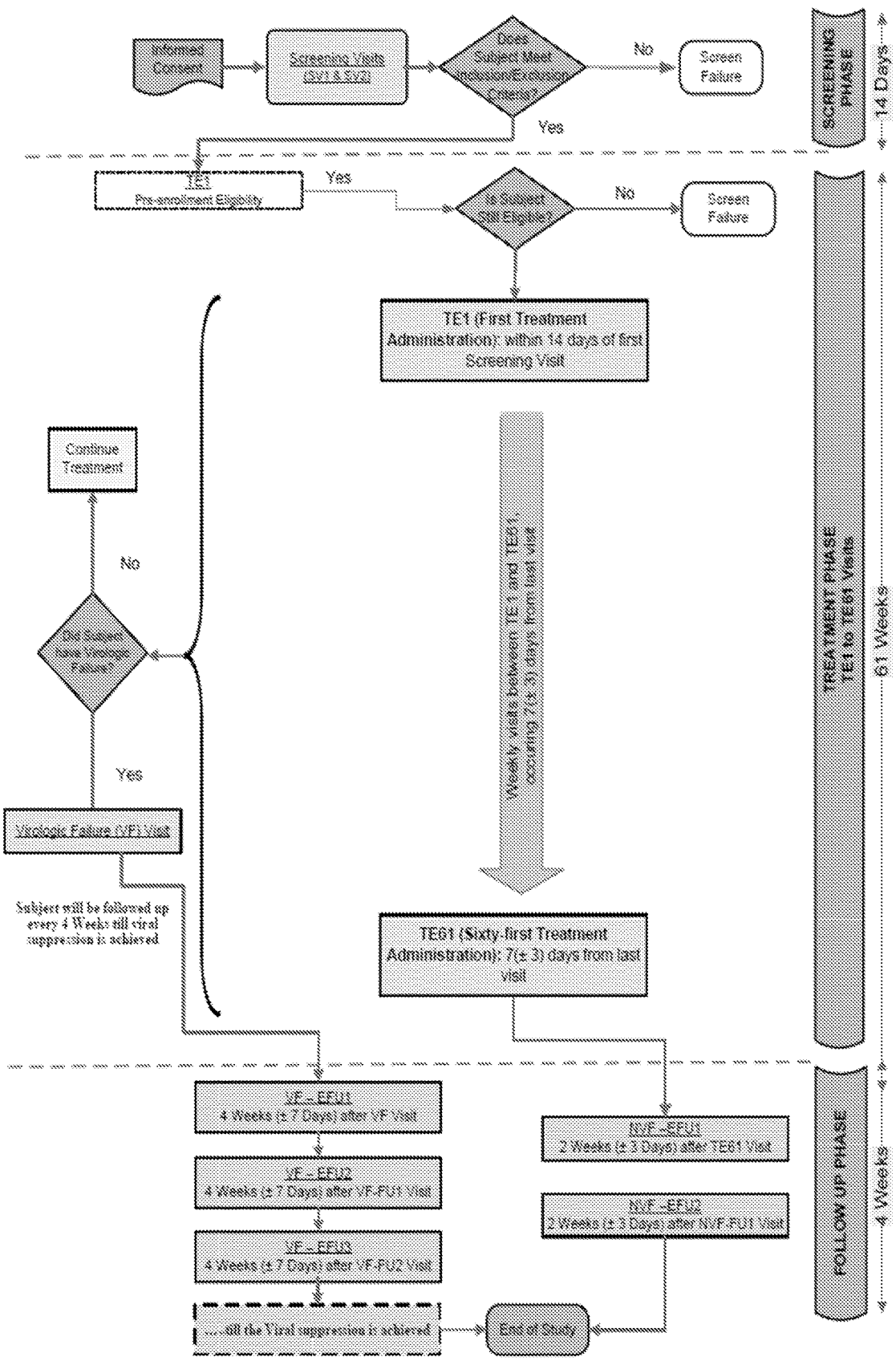
FIG. 15 shows the general study flow diagram for the second Phase 2b treatment substitution extension study.

Eligible subjects receive up to 61 treatments, given every week (±3 days) or until virologic failure, whichever occurs first. Treatment Extension Phase visits commenced on TE1, i.e. the date of first treatment, with weekly visits (±3 days) thereafter. See FIG. 15. As with the first TS study, only subjects with exclusive CCR5-tropic virus were to be enrolled. However, 6 out of 16 subjects were determined to have dual- or mixed-tropic (D/M) virus when screening blood samples were tested by HIV-1 Co-receptor Tropism by Proviral DNA method or Ultradeep Sequencing with Reflex (Quest Diagnostics), as a retrospective exploratory analysis.

Efficacy assessments at each week include assessment of viral load and CD4 cells count. Safety assessments consist of physical exam, lab, and adverse event assessments at each Treatment Extension and Follow-Up Visits.

Subject inclusion and exclusion criteria for the second Phase 2b extension TS study were similar to the criteria used for the first TS study.

PRO 140 350 mg is administered as subcutaneous injection in the abdomen weekly. A total of 350 mg (175 mg/mL) is delivered as two 1 mL injections on opposite sides of the abdomen. PRO 140 is provided to the administering personnel in single-use syringes prepared from vials of study drug stored at 2-8° C. at the site pharmacy prior to use. Each of two syringes is filled to deliver 1.0 mL of study drug. Equivalent volumes of study drug will be administered subcutaneously on opposite sides of the abdomen. A 25-gauge needle should be used to remove contents from vial and for administration to subjects. Contents should be administered slowly over 15 seconds per mL.

It is preferred that the same injection site be used throughout the study. At the same time, it is not recommended to inject the study drug into areas where skin shows signs of a previous injection site reaction. It is advised to change the injection site if any previous injection site reaction remains unresolved.

SC and IV injections of concentrated protein materials can be associated with injection-related AEs that impact the ability to safely and successfully deliver the drug. Local injection-site reactions may include pain/discomfort, induration, erythema, nodules/cysts, pruritus, ecchymosis, etc. For SC injections, bleeding, absorption of the drug, leakage of drug, and induration at the local injection site can be additional complications. Other AEs that are common to monoclonal antibody-based therapies are chills, headache, backache, malaise, fever, pruritus, rash, nausea, tingling, and hypertension.

Two (2) virologic failure subjects received a waiver to continue in Treatment Extension Phase and did not reinitiate ART. The other two virologic failure subjects did reinitiate ART and have achieved viral suppression to 'Non Detectable' or <50 HIV-1 RNA copies/ml.

Table 11 highlights the Sixteen (16) subjects in the Extension study. Out of these 16 subjects, ten (10) subjects have completed a total of more than 20 weeks of PRO 140 Monotherapy under both the first TS study and second TS Extension studies. The status of each subject is provided. Four (4) out of 16 subjects (25%) experiencing virologic failure. Of these 4 subjects, 2 subjects were found to have Dual- or Mixed-tropic virus, and 2 subjects were found to have exclusive CCR5-tropic virus. Two (2) virologic failure subjects received a waiver to continue in Treatment Extension Phase and did not reinitiate ART. The other two virologic failure subjects did reinitiate ART and have achieved viral suppression to 'Non Detectable' or <50 HIV-1 RNA copies/ml.

TABLE 11

Summary of Virologic Failure, CCR5- plus Dual/Mixed-tropic Population

| Parameter | Total (N = 16) n/N | CCR5 (N = 10) n/N (%) | D/M (N = 6) n/N (%) |
|---|---|---|---|
| Proportion of Subjects with Virologic Failure within 24 weeks of PRO 140 Monotherapy | 4/16 | 2/10 (20.0%) | 2/6 (33.3%) |

N = number of CCR5- plus Dual/Mixed-tropic subjects within the population
n = number of subjects (or observations) within the population Thus, interim study results show that 14 out of 16 subjects receiving greater than 20 weeks of monotherapy (time on monotherapy includes duration continuing from PRO 140 Substitution study). See Table 12, below.

TABLE 12

| Subject Number | Last Study Visit Completed | Time on PRO 140 Monotherapy* (# of weeks) |
|---|---|---|
| 1 | TE17 | 28 |
| 2 | TE18 | 29 |
| 3 | TE15 | 26 |
| 4 | TE16 | 27 |
| 5 | TE16 | 27 |
| 6 | TE17 | 28 |
| 7 | TE20 | 31 |
| 8 | TE11 | 22 |
| 9 | TE16 | 27 |
| 10 | TE13 | 24 |
| 11 | TE11 | 22 |
| 12 | TE11 | 22 |
| 13 | TE11 | 22 |
| 14 | TE11 | 22 |

All subjects enrolled in PRO 140 Substitution and PRO 140 Extension that experience virologic failure after initiating PRO 140 monotherapy have lab samples collected to assess viral phenotype using PhenoSense® Entry Assay (Monogram Biosciences). Outgrown HIV-1 RNA virus was exposed to three different compounds (AMD3100, maraviroc and PRO 140) to determine whether there is any change in Inhibitory Concentration ($IC_{50}$) during the course of the study. Furthermore, lab samples obtained for all 40 enrolled subjects at the Screening Visit for the PRO 140 Substitution study was analyzed as baseline data.

Complete PhenoSense® Entry Assay data for the PRO 140 Substitution study indicate that no significant change to the HIV-1 RNA virus or $IC_{50}$ values occurred as a result of exposure to PRO 140 monotherapy for the 18 subjects with virologic failure.

All subjects enrolled in PRO 140 Substitution and PRO 140 Extension have lab samples collected at various time points to assess whether anti-idiotypic antibodies (ADA) developed as a result of exposure to PRO 140 monotherapy. For the PRO 140 Substitution study, lab samples were taken at Screening Visit, Treatment Visits 4, 8, 12 and 14, VF Visit as well as the fourth week of the Follow-up Phase.

Similar to the ADA assessment, lab samples were collected at Screening Visit, Treatment Visits 4, 8, 12 and 14, and VF Visit to assess the pharmacokinetic (PK) properties of PRO 140 when administered as monotherapy during the PRO 140. Based on available results, PRO 140 has a favorable PK profile similar to that seen in prior clinical studies.

Subjects participating in the PRO 140 Extension study complete the same assessments at similar time points (Screening Visit 1, Treatment Extension Visits 4, 8, 12, 16, 20 and 24, VF Visit). Only ADA was assessed at the fourth week of the Follow-up Phase.

Additional studies have been ongoing and produced evidence that treatment substitution using PRO 140 monotherapy is effective for some patients for at least up to 11 months. That is, an ongoing extension study of PRO 140 monotherapy in HIV-infected patients has shown complete viral-load suppression for nearly 11 months. It is believed that complete virologic suppression through treatment substitution with a single agent, rather than through the widely used HAART combination therapy, could present a significant opportunity to treat HIV infection.

Based on the available data obtained from these studies, additional studies to further assess suppression of HIV-1 replication following addition of PRO 140 to currently approved anti-retroviral treatment in adult subjects with HIV-1 infection that cannot achieve suppression with current modalities are warranted.

The invention claimed is:

1. A method for treating an HIV-1 infected subject comprising:
    administering PRO 140 or a fragment thereof as a treatment substitution monotherapy;
    preventing virologic failure during treatment substitution monotherapy for a time period greater than four weeks;
    wherein the HIV-1 infected subject is stable on combination antiretroviral therapy prior to initiation of the treatment substitution monotherapy; and
    wherein the HIV-1 infected subject receives PRO 140 or a fragment thereof as a treatment substitution monotherapy for a period of at least one year.

2. The method of claim 1, wherein the HIV-1 infected subject has either CXCR4-tropic virus or dual/mixed tropic (R5X4) virus.

3. The method of claim 1, wherein PRO 140 is administered either intravenously or subcutaneously.

4. The method of claim 1, wherein PRO 140 is administered subcutaneously in an amount of 350 mg.

5. The method of claim 1, wherein PRO 140 is administered subcutaneously at a concentration of 175 mg/mL.

6. The method of claim 1, comprising administering PRO 140 one of once per week, once every two weeks, and once a month.

7. The method of claim 1, wherein the HIV-1 infected subject returns to combination antiretroviral therapy following PRO 140 treatment substitution monotherapy.

8. The method of claim 1, further comprising providing the HIV-1 infected subject during treatment substitution monotherapy with at least about a 60% likelihood of preventing virologic failure for a time period greater than four weeks.

9. A method for improving drug regime adherence by providing an HIV-1 infected subject with a treatment comprising:
    administering PRO 140 or a fragment thereof as a treatment substitution monotherapy;
    preventing virologic failure during treatment substitution monotherapy for a time period greater than four weeks;
    wherein the HIV-1 infected subject is stable on combination antiretroviral therapy prior to initiation of the treatment substitution monotherapy; and
    wherein the HIV-1 infected subject receives PRO 140 or a fragment thereof as a treatment substitution monotherapy for a period of at least one year.

10. The method for improving drug regime adherence of claim 9, comprising administering PRO 140 one of once per week, once every two weeks, and once a month.

11. The method for improving drug regime adherence of claim 9, wherein PRO 140 is self-administered subcutaneously in an amount of 350 mg.

12. A method for treating an HIV-1 infected subject with a treatment comprising:
    providing PRO 140 or a fragment thereof in a self-administrable dosage form;
    administering the PRO 140 or a fragment thereof as a treatment substitution monotherapy; and
    preventing virologic failure during treatment substitution monotherapy for a time period greater than four weeks;
    wherein the HIV-1 infected subject is stable on combination antiretroviral therapy prior to initiation of the treatment substitution monotherapy; and
    wherein the HIV-1 infected subject receives PRO 140 or a fragment thereof as a treatment substitution monotherapy for a period of at least one year.

13. The method for treating an HIV-1 infected subject of claim 12, further comprising testing the HIV-1 infected subject for virologic failure and resuming treatment with other anti-HIV drugs in the event of virologic failure.

* * * * *